United States Patent [19]

Lipton

[11] Patent Number: 5,747,545

[45] Date of Patent: May 5, 1998

[54] METHOD OF PREVENTING NMDA RECEPTOR COMPLEX-MEDIATED NEURONAL DAMAGE

[75] Inventor: Stuart A. Lipton, Newton, Mass.

[73] Assignee: The Children's Medical Center Corporation, Boston, Mass.

[21] Appl. No.: 407,973

[22] Filed: Mar. 22, 1995

Related U.S. Application Data

[63] Continuation of Ser. No. 25,028, Mar. 2, 1993, Pat. No. 5,455,279, which is a continuation-in-part of Ser. No. 949,342, Sep. 22, 1992, Pat. No. 5,234,956, and Ser. No. 939,824, Sep. 3, 1992, Pat. No. 5,334,618, which is a continuation-in-part of Ser. No. 680,201, Apr. 4, 1991, abandoned, said Ser. No. 949,342, is a continuation of Ser. No. 688,965, Apr. 19, 1991, abandoned.

[51] Int. Cl.[6] ........................ A61K 31/55
[52] U.S. Cl. ............... 514/742; 436/503; 514/289; 514/294
[58] Field of Search ............... 514/656, 659, 514/662, 724, 289, 294, 742; 436/503

[56] References Cited

U.S. PATENT DOCUMENTS

| | | |
|---|---|---|
| 3,328,251 | 6/1967 | Smith . |
| 3,391,142 | 7/1968 | Mills et al. . |
| 4,064,139 | 12/1977 | Anderson et al. ........ 548/425 |
| 4,122,193 | 10/1978 | Scherm et al. . |
| 4,273,774 | 6/1981 | Scherm . |
| 4,351,847 | 9/1982 | Griffith et al. . |
| 4,374,838 | 2/1983 | Anderson et al. ........ 514/289 |
| 4,399,141 | 8/1983 | Anderson et al. ........ 514/294 |
| 4,806,543 | 2/1989 | Choi . |
| 4,888,347 | 12/1989 | Woodruff et al. ........ 514/289 |
| 5,061,703 | 10/1991 | Bormann et al. . |
| 5,264,371 | 11/1993 | Miljanich et al. ........ 436/503 |
| 5,521,215 | 5/1996 | Mechoulam et al. ........ 514/454 |
| 5,559,095 | 9/1996 | Miljanich et al. ........ 514/12 |

OTHER PUBLICATIONS

Merck Index, Rimantadine, No. 8116, p. 1188.
Merck Idex, Memantine, No. A8, p. APP-2.
Merk Index, Amantadine, No. 373, p. 55.
Turski et al., Nature, 349:414–418.
Kornhuber et al., European Journal of Pharmacology, 166:589–550, 1989.
Borman, European Journal of Pharmacology, 166:591–592, 1989.
Muller, SCRIP 1515, p. 28 (1990).
Tominack and Hayden, Rimantadine and Hydrochloride and Amantadine Hydrochloride, pp. 460–461.
Braunwald et al., Principles of Internal Med. 11th ed. (N.Y. McGraw Hill 1987) pp. 1392–1396 & 2017–2019.
Hahn et al., Proc. Nat'l. Acad. Sci. USA 85:6556–6560 (1988).
Choi et al., Neuron 1:623–634 (1988).
Turski, Arzneim–Forsch./Drug Res. 40(I). Nr. 5 (1990).
Meldrum et al., Trends in Parm. Sciences 11:379–387 (1990).
Rothman et al., Trends in Neurosci. 10:299–302 (1987).

Primary Examiner—George F. Lesmes
Assistant Examiner—Robert H. Harrison
Attorney, Agent, or Firm—Fish & Richardson P.C.

[57] ABSTRACT

Disclosed is a method for decreasing NMDA receptor-mediated neuronal damage in a mammal by administering to the mammal a nitroso-compound that generates nitric-oxide or related redox species, in a concentration effective to effect neuroprotection. Also disclosed is a method for decreasing NMDA receptor-mediated neuronal damage in a mammal by administering to the mammal a nitroso-compound that generates nitric oxide (or a related redox species such as NO⁻ or NO⁺ equivalent), or a physiologically concentration effective to cause such neuroprotection.

1 Claim, 7 Drawing Sheets

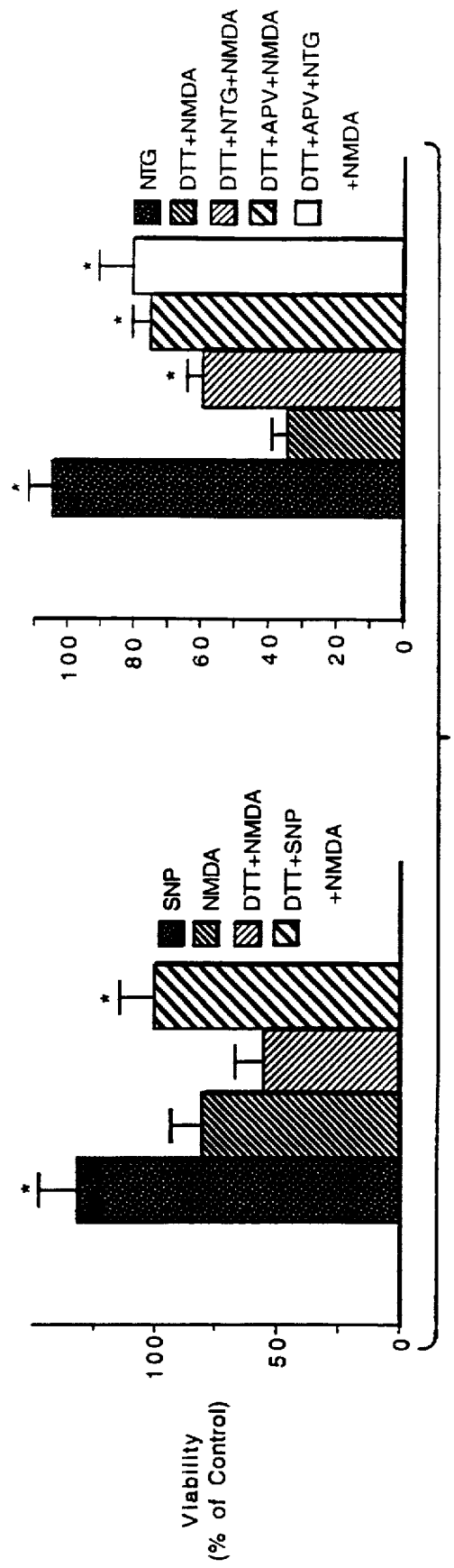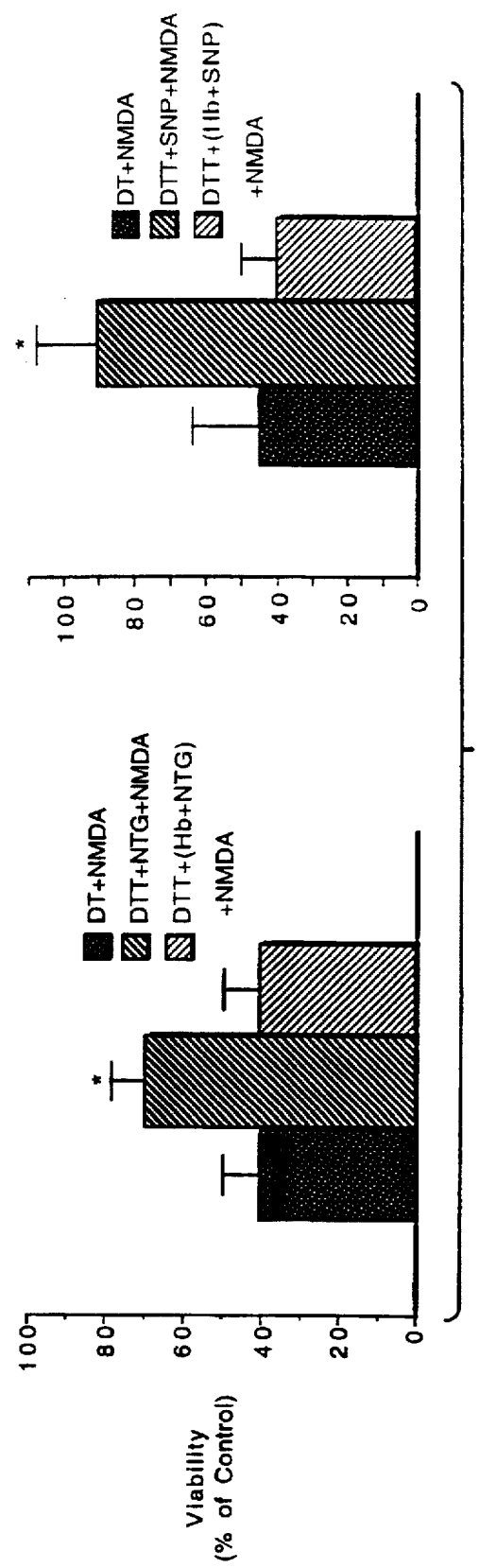
FIG. 6C
FIG. 6D

METHOD OF PREVENTING NMDA RECEPTOR COMPLEX-MEDIATED NEURONAL DAMAGE

BACKGROUND OF THE INVENTION

This application is a continuation of application U.S. Ser. No. 08/025,028, filed Mar. 2, 1991, now U.S. Pat. No. 5,455,279 which is a continuation in part of Ser. No. 07/949,342, filed Sep. 22, 1992, U.S. Pat. No. 5,234,956 and of U.S. Ser. No. 07/939,824, filed Sep. 3, 1992, U.S. Pat. No. 5,334,618 the former being a continuation of U.S. Ser. No. 07/688,965, filed Apr. 19, 1991, abandonded and the latter being a continuation-in-part of Ser. No. 07/680,201, filed Apr. 4, 1991 abandonded.

This invention relates to the treatment of nervous system disorders, particularly disorders mediated by the N-methyl-D-aspartate (NMDA) subtype of excitatory amino acid receptor complex.

Glutamate or related congenors have been implicated as a significant factor in the neurotoxicity associated with hypoxic-ischemic encephalopathy, anoxia, hypoglycemia, seizures, trauma, and several degenerative neurological disorders (Hahn et al., *Proc. Natl. Acad. Sci. USA* 85:6556, 1988; Choi, *Neuron* 1:623, 1988; Rothman et al., *Trends Neurosci.* 10:299, 1987; Meldrum et al., *Trends Pharm. Sci.* 11:379, 1990). In many central neurons the predominant form of this neurotoxicity appears to be mediated by activation of the NMDA subtype of glutamate receptor and subsequent influx of excessive $Ca^{2+}$ (Choi, *ibid*; Weiss et al., *Science* 247:1474, 1990). Lei et al. *Neuron* 8:1087–1099 (1992) discloses the use of nitroso-compounds (compounds containing the NO group) to treat neurological diseases. Stamler et al. *Science* 258:1898–1902 (1992) by referencing Lei et al. (1992) also discloses the use of nitroso-compounds to treat neurological diseases.

SUMMARY OF THE INVENTION

I have discovered that certain compounds protect neurons against NMDA receptor-mediated neuronal damage. Specifically, nitroglycerin, nitroprusside, and their nitroso-compound derivatives provide such protection. Thus, one aspect of the invention features a method for decreasing NMDA receptor complex-mediated neuronal damage in a mammal by administering one of the above-described compounds to the mammal, in a concentration effective to decrease such damage.

With regard to the compounds of the first aspect of the invention, I do not wish to bind myself to any particular theory or mechanism of action. However, it appears that oxidation of the thiol group(s) of the NMDA receptor's redox modulatory site protect against NMDA receptor-mediated neuronal damage. It is also known that the active species of nitroglycerin and nitroprusside is nitric oxide or related NO redox species.[1] See, e.g., Garthwaite et al. (*Trends in Neurosciences* 14:60, (1991). One possible mechanism for the protective effect that I have discovered is NO-induced oxidation of the NMDA receptor-channel complex, probably mediated by a nitrosation reaction involving transfer of the NO group to the thiol(s) of the NMDA receptor's redox modulatory site, resulting in an RS-NO ($NO^+$ equivalent). Similarly, the redox species nitroxyl anion ($NO^-$) can also react with thiol groups. In contrast, under physiological conditions, NO• (nitric oxide) reacts directly with thiol groups poorly, if at all.

[1] I use the term NO (nitrogen monoxide) to include the related redox species, i.e., NO• (nitric oxide), $NO^+$ (nitrosonium ion), and $NO^-$ (nitroxyl anion). See Stamler et al., cited above.

A second aspect of the invention features a method for decreasing NMDA receptor complex-mediated neuronal damage by administering a nitroso-compound, in a concentration effective to cause neuroprotection—e.g., a decrease in such damage. Without wishing to bind myself to a specific mechanism of action, it appears that NO or a related redox species acts on the thiol group(s) of the redox modulatory site of the NMDA receptor-channel complex to protect against NMDA receptor-mediated damage.

In preferred embodiments of both aspects of the invention, the mammal is a human patient infected with a virus affecting the nervous system—e.g., measles or human immunodeficiency virus (HIV). In particular, the patient being treated may be infected with HIV and may manifest symptoms of the AIDS related complex or acquired immunodeficiency syndrome (for example neurological manifestations of HIV (see, e.g., U.S. Ser. No. 571,949), such as those that may be treated according to the present invention, including, but not limited to, AIDS dimentia complex or cognitive-motor-sensory deficits of incipient or progressing dementia). Other neuro-degenerative states that can be treated according to the invention include Alzheimer's disease, Huntington's disease, amyotrophic lateral sclerosis (ALS or motor neuron disease), Parkinson's disease, neurolathyrism, Guam disease, and those listed in table 2, below. Alternatively, the patient may have (or be likely to be subject to) an acute disorder such as hypoxia, anoxia, carbon monoxide poisoning, ischemia, CNS trauma, hypoglycemia, seizures, stroke (by which I mean to include stroke associated with ischemia or subarachnoid hemorrhage), domoic acid poisoning, lead poisoning, or other acute disorders listed on Table 1, below. Where the patient is likely to be subject to one of the above conditions, the patient could be treated prophylactically according to the invention. Other diseases mediated (at least in part) by excitatory amino acid toxicity and can be treated by NMDA receptor complex modulation according to the present invention. Such diseases include: 1) ALS (amyotrophic lateral sclerosis or motor neuron disease); 2) painful types of "peripheral neuropathy" which may be mediated by excessive glutamate (NMDA) receptor stimulation, e.g., causalgia and other types of neuropathic pain syndromes, including painful types of peripheral neuropathy which may (but need not necessarily) include a central nervous system component.

By "NMDA receptor-mediated neuronal damage" is meant any neuronal injury which is associated with stimulation or co-stimulation of the NMDA receptor-channel complex, a receptor-channel complex which is found on a subset of mammalian neurons and which includes a binding site for a molecule such as glutamate, NMDA, or similar agonists (see below). Activation of this receptor-channel complex by binding agonists induces neuronal excitation by opening specific ion channels in the membrane.

By a "nitroso-compound" is meant any compound which produces a sufficient amount of NO (most probably a related redox species such as an $NO^+$ or $NO^-$ equivalent) upon administration to a mammal to decrease neuronal damage or injury. For convenience, I have also used the less precise term "NO-generating compound" to include compounds that produce the above described NO-related redox species (e.g., RS-NO, an $NO^+$ equivalent, or $NO^-$) or a physiologically acceptable salt thereof.

Useful compounds of the second aspect of the invention include any nitroso-compound. Verification that a particular compound provides protective oxidation of the NMDA receptor itself is a step well understood by those skilled in the art (see, e.g., Lipton, PCT WO 91/02810).

The two preferred compounds of the first aspect of the invention (i.e., nitroglycerin and sodium nitroprusside) provide the advantage of a proven record of safe human administration (i.e., for treatment for cardiovascular disorders). Other nitroso-compounds that can be used in the method of the invention include: isosorbide dinitrate (isordil); S-nitroso captopril (Snocap); Serum albumin coupled to nitric oxide ("SA-NO"); Cathepsin coupled to nitric oxide (cathepsin-NO); tissue plasminogen activator coupled to NO (TPA-NO); SIN-1 (or molsidomine) cation-nitrosyl complexes, including $Fe^{2+}$-nitrosyl complexes; Nicorandil; S-nitrosoglutathione; NO coupled to an adamantine derivative, including memantine (see U.S. Pat. No. 5,334,618 the specification of which is hereby reproduced in its entirety in Appendix A, except that page numbers and figure numbers have been re-formatted to avoid duplication. S-nitrosothiols including S-nitrosocysteine; quinones, including pyrroloquinoline quinone (PQQ), ester derivatives of PQQ, or ubiquinone; sydnonimins or nonoates having the formula

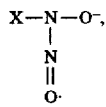

where X is any nucleophile including an amine; and agents which generate an oxidizing cascade similar to that generated by $N^2$ such as α-lipoic acid (thioctic acid and its enantiomers); dihydrolipoate; glutathione; ascorbate; and vitamin E.

[2] Without wishing to be bound to a specific theory, such cascades are characterized by electron exchange with nitros-compounds.

Any of the above described nitroso-compounds may be combined with other redox compounds that facilitate production and maintenance of NO. For example, direct NO-generators can be combined with pyroloquinoline quinone (PQQ), a known NMDA redox modulator (see U.S. Pat. No. 5,091,391), or PQQ's derivative esters, or other quinones such as ubiquinone.

Regarding compounds according to the second aspect of the invention, the ability of NO to be transported to and cross cell membranes facilitates therapies according to the invention.

A third aspect of the invention is based on the recognition that the redox species NO• (nitric oxide containing one free electron) leads to neurotoxicity via formation of peroxynitrite ($ONOO^-$) (or its decomposition products) by reaction with $O_2^{•-}$ (see FIG. 7, below for demonstration). Applicant notes that the literature describes the enzyme, NO synthase, which produces nitric oxide in certain cell types; this enzyme and its role in neuronal function is discussed in, e.g., Garthwaite et al. (*Trends in Neurosciences* 14:60, 1991), Hope et al. (*Proc. Natl. Acad. Sci. USA* 88:2811, 1991), and Dawson et al., (*Ann. Neurol.* 32:297-311, 1992). According to this third aspect of the invention, nitric oxide synthase is inhibited to effect neuroprotection. This aspect of the invention features administering inhibitors of nitric oxide sythase to decrease the availability of NO• and hence decrease the availability of neurotoxic peroxynitrite ($ONOO^-$). This aspect of the invention may be combined with the first two aspects of the invention or the nitric oxide syntase inhibitor may be administered independently to treat neurological manifestations of infection with an HIV, to treat neuropathic pain mediated by NMDA teceptor activity, or to treat ALS.

A fourth aspect of the invention features the recognition that neuroprotective dosages of nitrosocompounds can lower blood pressure as an undesirable side effect in naive patients, but that it is possible to build tolerance to this side effect without losing the desired neuroprotective effect. Accordingly, the fourth aspect features administering a nitroso compound capable of protecting against NMDA receptor complex-mediated neuronal injury, continuously over an extended period with gradually escalating dosage, beginning at a dosage level which does not substantially reduce the patient's blood pressure, and increasing to a later dosage level to systemic tolerance of the compound. The later dosage level is high enough to substantially reduce a naive patient's blood pressure, but the continuous administration of the compound builds tolerance to the compound's blood-pressure lowering effect, so that the later dosage level does not in fact substantially reduce the patient's blood pressure.

Nitroglycerin is the preferred compound for the fourth aspect of the invention. It may be administered by transdermal patch as described in detail below (e.g. a patch having a surface area over 50 $cm^2$). Preferably such administration is continous over a period exceeding 24 hours.

It is also useful, when acutely administering a nitroso compound according to the first two aspects of the invention, to co-administer a blood-pressure increasing compound such as dopamine.

A fifth aspect of the invention features the administration of superoxide dismutase (SOD), catalase, or both, to limit neurotoxicity by decreasing the formation of peroxynitrite from the reaction of NO• with superoxide anion ($O_2^{•-}$). The treatment can be adjunctive with the first two aspects of the invention or it can be used independently, particularly to treat neurological manifestations of infection with HIV or of ALS. Polyethylene glycol (PEG) is used to enhance absorption into the central nervous system (CNS) and efficacy of SOD and/or catalase. An SOD mimic, the protein-bound polysaccharide of *Coriolus versicolor* QUEL, termed "PS-K", may also be effective by parenteral or oral routes of administration, especially with PEG to enhance CNS absorption, and such mimics may be substituted for SOD in this aspect of the invention. See Kariya et al., *Mol. Biother,* 4:40–46 (1992); and Liu et al., (1989) *Am. J. Physiol.* 256:589–593.

Other features and advantages of the invention will be apparent from the following detailed description and from the claims.

DETAILED DESCRIPTION

The drawings are first briefly described.

Drawings FIGS. 1–3 are graphs showing NMDA-evoked intracellular [$Ca^{2+}$] levels observed by fura-2 imaging over time as different redox agents including NTG are administered to cultured neurons. (See Examples 1 and 2.)

FIG. 4 is a graph showing NMDA-evoked currents (including [$Ca^{2+}$]) in cortical neurons and the effect of different redox agents including NTG. (See Example 3.)

FIG. 5A–B are graph showing NMDA-evoked intracellular [$Ca^{2+}$] induced in cortical neurons and the effect of different redox agents including S-nitrosocysteine (SNOC). (See Example 5.)

FIG. 6A–D are bar graphs showing that sodium nitroprusside (SNP) or nitroglycerin (NTG) prevents NMDA-mediated neurotoxicity.

FIGS. 7A and 7B are bar graphs showing superoxide requirement of neurotoxicity induced by S-nitrosocysteine (SNOC) or peroxynitrite ($ONOO^-$).

The present invention is based on the finding that the compounds nitroprusside and nitroglycerin decrease NMDA receptor complex-mediated neuronal damage (see below). This neuroprotection may be due to nitrosation or oxidation of the NMDA receptor at the redox modulatory site, resulting in NO group transfer to the thiol group(s) of the NMDA receptor's redox modulatory site to form an RS-NO (NO+ equivalent). This chemical reaction leads to a decrease in NMDA receptor-operated channel activation by excitatory amino acids (such as NMDA or glutamate) and a concomitant decrease in intracellular calcium influx and amelioration of neurotoxicity.

An increased level or effect of one or more glutamate-related compounds is associated with many neurodegenerative disorders (e.g., those listed above). In addition to glutamate itself, neuronal injury may result from stimulation of the NMDA receptor-channel complex by other excitatory amino acids, such as aspartate, quinolinate, homocysteic acid, cysteine sulfonic acid, cysteine, or from stimulation by excitatory peptides, such as N-acetyl aspartyl glutamate.

Nitroglycerin (1,2,3-propanetriol trinitrate or glyceryl trinitrate, abbreviated NTG or GTN), sodium nitroprusside, and NO-generating derivatives of either one of those compounds are considered to be particularly useful in the invention.

Compounds of the second aspect of the invention (i.e., nitroso-compounds or NO-generating compounds and their derivatives) may be tested for efficacy in decreasing neuronal damage using the assays described below—i.e. in assays of NMDA-evoked ionic current (see, e.g., PCT WO 91/02810), in assays of NMDA- evoked increases in intracellular $Ca^{2+}$ (see below), or in assays of neuronal cell death (see below). An effective compound will cause a decrease in ionic current, intracellular $Ca^{2+}$ concentration, or in neuronal cell death, respectively. Compounds most preferred in the invention are those which effect the greatest protection of neurons from NMDA receptor complex-mediated injury, e.g., that injury resulting from stimulation of the NMDA receptor by NMDA(as shown below) or other excitatory amino acids or stimulation by excitatory peptides, such as N-acetyl aspartyl glutamate.

Assay for Neuronal Cell Function and Death

To test compounds for their ability to prevent neurotoxicity, neuronal cell death may be assayed as follows. Neonatal cortical neurons were prepared according to the general method of Snodgrass et al. (1980) Brain Res. 190:123–138; and Rosenberg et al (1988) J. Neurosci. 8:2887-2899. Cultures are monitored following a brief exposure (5–30 minutes) to 30–100 µM NMDA, or to 5 mM DTT (for 5 minutes) followed by 30–100 µM NMDA (for 5–30 additional minutes), and overnight incubation (i.e., 16 to 24 hours). Experiments in vivo suggest that a transient chemical reducing state exists in the brain following stroke; the introduction of the chemical reducing agent DTT may mimic this reducing environment, increasing the similarity of the in vitro assay to the in vivo situation. The candidate compound is tested by addition (e.g., in a series of concentrations ranging from 0.1 nM-10 mM) after DTT treatment but before NMDA treatment. The candidate compound can be added for minutes, hours, or even days prior to its washout period. Following NMDA exposure, the cultures are incubated an additional 16–24 h at 37° C. in an atmosphere of 5% $CO_2$/95% air. Neuronal cultures are scored for cell survival after this overnight incubation because NMDA toxicity is often delayed by several hours following NMDA exposure. The ability of cortical neurons to maintain phase-bright appearance and exclude trypan blue is used as an index of survival (Rosenberg et al., Neurosci. Lett. 103: 162–168, 1989).

Measurement of Intracellular $Ca^{2+}$

The concentration of intracellular free $Ca^{2+}$ ($[Ca^{2+}]i$) is measured in neonatal cortical neurons by digital imaging microscopy with the $Ca^{2+}$ sensitive fluorescent dye fura 2, as follows. The same cortical neuronal cultures as described above are used. During $Ca^{2+}$ measurements, unless otherwise stated the fluid bathing the neurons consists of Hanks' balanced salts: 137.6 mM NaCl, 1 mM $NaHCO_3$, 0.34 mM $Na_2HPO_4$, 0.44 mM $KH_2PO_4$, 5.36 mM KCl, 1.25 mM $CaCl_2$, 0.5 mM $MgSO_4$, 0.5 mM $MgCl_2$, 5 mM Hepes NaOH, 22.2 mM glucose, and sometimes with phenol red indicator (0.001% v/v); pH 7.2. NMDA (in the absence $Mg^{++}$), glutamate, and other substances are usually applied to the neurons by pressure ejection after dilution in this bath solution. Neuronal $[Ca^{2+}]i$ is analyzed with fura 2-acetoxymethyl ester (AM) as described [Grynkiewicz, et al., J. Biol. Chem. 260:3440 (1985); Williams et al., Nature 318:558 (1985); Connor et al., J. Neurosci. 7:1384 (1987); Connor et al., Science 240:649 (1988); Cohan et al., J. Neurosci. 7:3588 (1987); Mattson, et al., ibid, 9:3728 (1989)]. After adding Eagle's minimum essential medium containing 10 µM fura 2-AM to the neurons, the cultures are incubated at 37° C. in a 5% $CO_2$/95% air humidified chamber and then rinsed. The dye is loaded, trapped, and deesterified within 1 hour, as determined by stable fluorescence ratios and the effect of the $Ca^{2+}$ ionophore ionomycin on $[Ca^{2+}]i$ is measured. During $Ca^{2+}$ imaging, the cells are incubated in a solution of Hepes-buffered saline with Hanks' balanced salts. The $[Ca^{2+}]i$ is calculated from ratio images that are obtained by measuring the fluorescence at 500 nm that is excited by 350 and 380 nm light with a DAGE MTI 66 SIT or QUANTEX QX-100 Intensified CCD camera mounted on a Zeiss Axiovert 35 microscope. Exposure time for each picture is 500 ms. Analysis is performed with a Quantex (Sunnyvale, Calif.) QX7-210 image-processing system. Since cells are exposed to ultraviolet light only during data collection (generally less than a total of 20 s per cell), bleaching of fura 2 is minimal. Delayed NMDA-receptor mediated neurotoxicity has been shown to be associated with an early increase in intracellular $Ca^{2+}$ concentration.

Patch-Clamp Recording

Patch-clamp recordings were performed in the whole-cell configuration generally using the procedure described by Hamill et al. (1981) as modified by Lipton and Tauck (1987); and Aizenman et al. (1988). Patch-clamp pipettes typically contained 140 mM KCl (or 120 mM CsCl and 20 mM TEA-Cl), 2 mM $MgCl_2$, 2.25 mM EGTA, 10 mM HEPES-NaOH (pH 7.2). Redox reagents were administered by superfusion (3.5 ml/min), while NMDA and glycine were always coapplied by puffer pipette.

A compound may be tested for utility in the method of the invention using any type of neuronal cell from the central nervous system, as long as the cell can be isolated intact by conventional techniques. Although cortical neuron cultures are used above, retinal ganglion cell neurons, spinal cord neurons, cerebellar granular neurons, or any neuron containing NMDA receptors (e.g., neurons from other regions of the cortex) may also be used. Such neurons may be prenatal or postnatal.

The following examples illustrate compounds useful in the method of the invention and their efficacy in reducing neuronal damage. These examples are provided to illustrate the invention and should not be construed as limiting.

EXAMPLE 1–4

NTG or SNP Inhibits NMDA-Induced Increases in $[Ca^{++}]$ in Rat Cortical Neurons in Culture.

In this experiment, the effect of NTG on intracellular $[Ca^{++}]$ increases induced by NMDA were followed using digital $[Ca^{++}]$ imaging techniques, based on the dye fura-2.

Specifically, the model for NMDA-mediated neurotoxicity involves exposure of cultured rat cortical neurons to NMDA in the presence of glycine (a co-agonist). NMDA (50 µM) induces an increase in $[Ca^{++}]_i$ (intracellular calcium ion concentration) that is further enhanced after exposure to the strong reducing agent, dithiothreitol (DTT). Chemical reduction of the NMDA redox modulatory site thiol group(s) with DTT increases the neurotoxic effect of NMDA.

Antagonism of NMDA receptor-mediated neurotoxicity by NTG is demonstrated as follows.

Cortical cultures were derived from embryonic (fetal day 15 or 16) Sprague-Dawley rats as described previously (Dichter, 1978; Rosenberg and Aizenman, 1989). Briefly, following dissociation in 0.027% trypsin, cerebral cortical cells were plated at a density of $4.5 \times 10^5$ per 35 mm dish containing poly-L-lysine-coated glass coverslips in Dulbecco's modified Eagle's medium with Ham's F12 and heat-inactivated iron-supplemented calf serum (Hy-Clone) at a ratio of 8:1:1. After 15 days in culture (when the astrocyte layer had become confluent), the cultures were treated with cytosine arabinoside for 72 hr. The culture medium was replenished 3 times weekly. Cultures were incubated at 36° C. in a 5% $CO_2$, 95% air humified atmosphere. The cultures were used for experiments at room temperature (21° C.–24° C.) approximately 1 month after plating. Neurons could be reliably identified by morphological criteria under phase-contract optics, as later confirmed by patch-clamp recording.

To permit physiology experiments ($Ca^{2+}$ imaging or patch clamping) under normal room air conditions, just prior to a recording session the culture medium was exchanged for a solution based on Hanks' balanced salts (as defined above with 1.25–2.5 mM $CaCl_2$). To enhance physiological responses to NMDA, the saline was nominally $Mg^{2+}$ free and contained 1 µM glycine, a coagonist required for NMDA receptor activation (Johnson and Ascher, 1987; Kleckner and Dingledine, 1988). Tetrodotoxin (1 µM) was added to block action potentials and ensuing neurotransmitter release from other neurons onto the cell of interest. The presence of intact neurotransmission might have obfuscated the results if, for example, high $K^+$, kainate, or NMDA caused the release of a substance from one neuron that in turn acted on the cell being monitored.

FIG. 1 shows quantifications of $[Ca^{2+}]_i$, from digital representations of fura-2 images over time for five cortical neurons in the field being imaged. DTT, NTG, DTNB (5,5dithio-bis-2-nitrobenzoic acid) were applied (in that order) for approximately 2 minutes and washed out prior to data collection of NMDA-evoked $[Ca^{2+}]_i$ responses. These data were collected immediately following exposure to 50 µM NMDA.

In FIGS. 1 and 2, the NMDA-induced $[Ca^{2+}]_i$ response after DTT pretreatment was set at 100%. Prior to DTT pretreatment, the NMDA-induced $[Ca^{2+}]_i$ response was about 68%. Following DTT, subsequent NTG or SNP treatment decreased the NMDA-evoked $[Ca^{2+}]_i$ response to 60% or less. The strong oxidizing agent DTNB also decreased the NMDA evoked $[Ca^{2+}]_i$ responses. Subsequent treatment with DTT restored the NMDA-evoked $[Ca^{2+}]_i$ response to 100%.

EXAMPLE 2

Cortical cultures were prepared as described in Example 1 and were pretreated with DTT, washed, and treated with 100 µM NTG, followed by 50 µM NMDA. In FIG. 3, NTG persistently decreased the NMDA-evoked $[Ca^{2+}]_i$ response, and this decrease persisted through repeated readministration of NMDA. Readministration of DTT reversed the effect of NTG.

EXAMPLE 3

The cortical cultures described above were prepared as described in Examples 1 and 2, and patch clamp recordings were performed instead of digital $Ca^{2+}$ imaging. Specifically, NMDA (50 µM) was coapplied with glycine (1 µM) from a pneumatic pipette. Such application resulted in an inward current with the cell voltage clamped at a holding potential of −60 mV. A 2 min incubation in DTT (followed by washout) enhanced the NMDA-evoked current. This current was subsequently attenuated following a 2 min exposure to NTG (and washout). Reapplication of DTT (followed by washout) increased the current response to its previous value.

FIG. 4 illustrates sequential compilation of the peak NMDA-evoked currents for 18 cells following treatment (and subsequent washout) of each redox reagent listed on the abscissa. The temporal order of addition of the redox reagents is indicated on the abscissa. Values are mean ±SEM, normalized to the 50 µM NMDA response observed after exposure to DTT to permit comparison among several cells. Responses to NMDA that are statistically smaller than those previously obtained directly after DTT exposure are marked with an asterisk (P<0.001, ANOVA followed by Scheffé multiple comparison of means).

A 2 min exposure to DTT (2 mM, followed by washout) increased NMDA-activated currents, whereas the addition of NTG (500 µM, followed by washout) inhibited the responses. Subsequent incubation in DTNB (500 µM for 2 min, followed by washout) decreased the responses slightly.

EXAMPLE 4

The experiment of Example 3 was repeated using 1–5 mM NEM, N-ethylmalemide, an agent known to alkylate sulfhydryl (thiol) groups of proteins. Following alkylation, neither NTG nor DTNB significantly affected the amplitude of NMDA evoked current, indicating that the redox modulatory site of the NMDA receptor, the site reacting with the NO group, is comprised of a thiol group(s).

EXAMPLE 5

SNOC Decreases NMDA-Evoked $[Ca^2]_i$ Responses

S-nitrosocysteine (SNOC) both liberates NO˙ and participates in nitrosation ($NO^+$ equivalents reacting with protein thiol groups). FIG. 5A is a digital representation of fura-2 calcium images as described above, for 10 cortical neurons in a single field. Following each response to NMDA, $[Ca^{2+}]_i$ returned to the baseline value within 1 min (data not shown for clarity). The data points are connected by dashed lines merely to emphasize the temporal order of addition. In each case, 2 mM DTT was applied for ~2 min and then washed out prior to the application of NMDA and data collection. Values are mean ±SEM, normalized to the NMDA (50 µM) response obtained after exposure to DTT (maximum response ~750 nM $[Ca^{2+}]_i$).

Following maximal chemical reduction with DTT, the NMDA-evoked response was increased, but was subsequently inhibited by a 3 min exposure to 100 µM S-nitrosocysteine (SNOC). Following washout of S-nitrosocysteine, the NMDA-elicited response recovered only slightly. A second exposure to DTT fully reversed the inhibitory effect of S-nitrosocysteine. Responses to NMDA that are statistically smaller than those obtained directly after DTT exposure are marked with an asterisk (P<0.01, ANOVA followed by Scheffé multiple comparison of means). FIG. 5B shows that pretreatment with NEM blocks the effect of SNOC by alkylating thiol group(s), thus preventing transnitrosation of the NO group to NMDA receptor thiol(s).

EXAMPLE 6

Nitroglycerin (NTG) or Sodium Nitroprusside (SNP) Prevents NMDA Receptor-Mediated Neurotoxicity Using the neurotoxicity assay described above, the compounds sodium nitroprusside and nitroglycerin were tested individually for their ability to increase survival of neonatal cortical neurons. The neuronal cells were incubated for 16–24 hours at 37° C. in a humidified atmosphere of 5% $CO_2$ and 95% air.

As shown in FIG. 6A–6D, surviving neurons are expressed as the percentage of viable neurons in the control culture dishes in the same experiment. The concentrations of drugs were as follows: APV (2 mM), NTG (100 µM), SNP (400 µM), DTT (0.5–2 mM), and reduced Hb (500 µM). In experiments with NTG, cultures were exposed to 30 µM NMDA for 30 min; for the SNP experiments, exposure was to 75 µM NMDA for 5 min. For the experiments with Hb, NTG or SNP was preincubated with a chemically reduced, purified preparation of Hb prior to addition to the cultures. Values are mean ±SEM for experiments run in triplicate on sibling cultures on separate days (total of 32 experiments). Astericks indicate significant difference compared with the value for DTT-NMDA exposure, $P<0.05$ (ANOVA followed by Scheffe multiple comparison of means.

We found that either NTG or SNP ameliorated neuronal injury engendered by the addition of NMDA after exposure to DTT (FIGS. 6A and 6B). The latter compound was added to produce chemical reduction of the redox modulatory site in order to maximize NMDA-activated current, $[ca^{2+}]_i$ responses, and neurotoxicity (as reported in the literature). The fact that a supramaximally effective concentration of the NMDA receptor-specific antagonist APV (2 mM) in combination with NTG failed to prevent neuronal cell death to a greater degree than APV alone suggests that the lethal effects were mediated via the NMDA receptor (FIG. 6B). In addition, exposure to 500 µM reduced hemoglobin (Hb), which complexes NO, did not affect neuronal survival on its own under these conditions; however, Hb completely inhibited the effect of 100 µM NTG, signifying that the protective action was mediated by NO (FIG. 6C). Reduced Hb (500 µM) also completely inhibited the protective action of 400 µM SNP, again suggesting the involvement of NO (FIG. 6D). It is likely that at least a part of the neuroprotective effect of NO is derived from oxidation of the redox modulatory site, since this action has previously been shown to attenuate NMDA receptor-mediated neurotoxicity.

EXAMPLE 7
Superoxide Dismutase (SOD) Plus Catalase Can Prevent Neurotoxicity Mediated by Peroxynitrite (ONOO–) formed from the Reaction of Nitric Oxide (NO•) with Superoxide Anion ($O•_2^-$)

S-nitrosocysteine was added as a source of NO• to cerebrocortical cultures (Lei et al., (1992) Neuron 8:1087–1099; Stamler et al., (1992) Science 258:1898–1902). Incubation in this S-nitrosothiol (RS-NO) compound produced dose-dependent killing of cortical neurons. The neurotoxic effect of maximally-lethal concentrations of S-nitrosocysteine (200 µM) could be prevented by simultaneous addition of SOD and catalase (50 U/ml each) (FIG. 7A). These findings are consistent with the very rapid liberation of NO• ($t_{1/2 \, (pH \, 7.4)}$ of S-nitrosocysteine ~30 s) for reaction with endogenous $O_2•^-$ to form peroxynitrite (ONOO$^-$) with subsequent neuronal damage.

To test whether it is indeed peroxynitrite (and/or its decomposition products) that is neurotoxic, we next showed that purified OONO$^-$ kills neurons in a dose-dependent fashion. Peroxynitrite leads to lipid peroxidation and massive oxidation of sulfhydryls (Radi et al., (1991) J. Biol. Chem. 266:4244–4250; Radi et al., (1991) Arch. Biochem. Biophys. 288:481–487). In addition, as predicted if OONO$^-$ and/or its decomposition products were neurotoxic, reaction with SOD (Ischiropoulos et al., (1992) Arch. Biochem. Biophys, 298(2):431–436) and catalase did not prevent the lethal action of peroxynitrite on neurons (FIG. 7B). These experiments indicate that SOD and catalase might be useful adjunctive neuroprotective agents that could be administered with the nitroso-compounds, such as NTG and SNP, in order to prevent NMDA receptor-mediated neurotoxicity, because SOD plus catalase would prevent the formation of neurotoxic ONOO$^-$ from any NO• that might be formed by the addition of the exogenous nitroso-compounds.

The results of the above experiments, as shown in FIG. 7, depict the superoxide anion requirement of neurotoxicity induced by S-nitrosocysteine (SNOC) but not peroxynitrite (ONOO$^-$). A, B, Superoxide dismutase (SOD, 50 U/ml) plus catalase (cat, 50 U/ml) prevented neurotoxicity induced by SNOC (200 µM, B). Neuronal survival was not significantly affected in the presence of SOD/catalase alone compared to that observed in sibling control cultures. As an additional control, 200 µM SNOC that had been incubated at room temperature for several days, in order to release all NO species, did not result in neurotoxicity (A, far left columns, labeled "old SNOC"). Values are expressed as mean+s.e.m. (n=9). Statistical comparisons were performed by an analysis of variance followed by a Scheffe multiple comparison of means (*, $P<0.01$ compared to control; **, $P<0.05$ compared to control; †, $P<0.01$ compared to nitroso compound+SOD/catalase).

Specifically, the data in FIG. 7 were generated using mixed neuronal and glial cortical cultures from neonatal rats, as described previously (Lei, et al., (1992) Neuron 8:1087–1099). In at least three separate experiments, triplicate cultures were incubated overnight in Earle's buffered saline solution (EBSS) containing various concentrations of SNOC, peroxynitrite, SOD, catalase, or glutamate. Similar results were obtained, however, with 20 min incubations in peroxynitrite, consistent with the known rapid effects of this potent oxidizing agent. The culture fluid was assayed for lactase dehydrogenase (LDH) as an indicator of neuronal survival by measuring the absorbance at 450 nm (Koh et al., (1987) J. Neurosci. Meth. 20:83–90). The cultures were also scored for neuronal viability by cell counting, generally with 0.2% trypan blue, after fixation in 2.5% glutaraldehyde, as described above. Neurons from cultures grown on 15 mm diameter cover slips were counted in a masked fashion in ~30 microscopic fields at 200 x. Control cultures scored in this manner typically contained approximately 1000 viable neurons. Over the range of values illustrated here, there was a linear relationship between the neuronal cell counts and the LDH viability results, as determined by a standard curve based upon experiments with varying concentrations of glutamate (0–1 mM). For LDH assays, neuronal survival was normalized to that observed in control sibling cultures (100% viability value) and in the presence of 1 mM glutamate (0% viability value); values slightly below 0% were obtained by extrapolation but were not significantly different from 0%. Similar experiments on cultures of purified astrocytes (lacking neurons) did not produce changes in LDH.

Therapy

To prevent neuronal damage, compounds of the invention may be administered by any of a number of routes in an amount sufficient to attenuate an NMDA-evoked ionic current or a rise in $[ca^{2+}]i$, or neurotoxicity. The compound may be included in a pharmaceutical preparation, using a pharmaceutical carrier (e.g., physiological saline); the exact formulation of the therapeutic mixture depends upon the route of administration. Preferably, the compound is administered orally or intravenously, but it may also be administered sublingually, by nasal spray, by transdermal patch, subcutaneously, intraventricularly, intravitreally, or by ointment. The preferred compounds, nitroglycerin or their derivatives (including all those preparations commercially available, e.g., those listed in the *Physician's Desk Reference* (1991) under coronary vasodilators or under nitroglycerin or nitroglycerin intravenous and including isosorbide mononitrate, isosorbide dinitrate, nitroglycerin sublingual, Minitran, NT-1, Niotrocor, Nitroderm, Nitrodisc, Nitro-dur, Nitro-Dur II, Nitrofilm, Nitrogard, Nitroglin, Nitropen, Tridil, and 6-chloro-2-pyridylmethyl nitrate) are administered at 0.01 mg–60 gm/day, in divided doses. Sodium nitroprusside—$Na_2[Fe(CN)_5NO]\cdot 2H_2O$ (from Elkins-Sinn, Inc., Cherry Hill N.J.), Nipride (from Roche, Nutley, N.J.), or other preparations—are administered intravenously at 0.5–10 μg/min.

Other nitroso-compounds, determined to be an effective neuroprotective agent by the assays described herein, are administered as above, at a dosage suitable to reduce neuronal damage, or NMDA evoked ionic current or increased $[Ca^{2+}]i$. Generally, such compounds are administered in dosages ranging from 0.01 mg–60 gm/day, more preferably in dosage of 0.1–5 mg/day.

Those skilled in the art will understand that there are other factors which aid in determining optimum dosage. For example, for NO-conjugated drugs, the dosage used for the unconjugated drug (e.g. TPA a dosage of 0.35–1.08 mg/kg and generally ≦0.85 mg/kg) is predictive of useful NO-conjugate dosage. Dosages may be divided. Treatment may be repeated as necessary to prevent or alleviate neurological injury. It is desirable to maintain levels of NO or related redox species in the brain of 1 nM to 500 μM.

For the CNS-protective purposes described herein, nitroso-compounds such as NTG and SNP can be administered acutely along with pressor agents (e.g., dopamine) to prevent a drop in systemic blood pressure.

With specific reference to nitroglycerin (NTG), I have also determined that patients can be made tolerant to the undesired systemic effects of NTG (e.g. blood pressure drop, coronary artery dilation or headache), without building tolerance to the desired neuroprotective effect of NTG, e.g., in the brain, spinal chord, and retina. Therefore, it is advantageous to induce NTG tolerance by gradually increasing dosage, thus increasing the neuronal protective effect.

To illustrate the development of systemic tolerance, a human patient could be made tolerant by intravenous administration of NTG within 18–24 hr of continuous infusion (see for example, J. E. Shaffer, B. -A. Han, W. H. Chern, and F. W. Lee, J. Pharmacol. Exper. Therap., 1992;260:286–293; D. C. May, J. J. Popma, Wh. H. Black, S. Scahaffer, H. R. Lee, B. D. Levine, and L. D. Hillis, New Engl. J. Med. 1987;317:805–809; C. M. Newman, J. B. Warren, G. W. Taylor, A. R. Boobis, and D. S. Davis, Br. J. Pharmacol. 1990;99:825–829). Oral, nasal spray, or sublingual NTG could also be used to induce systemic tolerance.

Another, perhaps easier, method for making humans tolerant within 24 hours to the systemic effects of NTG is to administer nitroglycerin as nitropaste or as a transdermal patch for transdermal delivery, for instance, as follows: ½inch every 4 to 6 hours, while monitoring the blood pressure (to see when hypotension subsides from the applied nitropaste). As tolerated (e.g., in the absence of sudden drops in blood pressure), the dose of nitropaste is increased to up to 3 inches with each administration. Under these conditions, tolerance (as evidenced by no effect on systemic blood pressure) will develop in 18–24 hours or less. Nevertheless, the therapeutic effect of NTG on the brain's NMDA receptors to prevent excitotoxicity should be maintained under these conditions.

An animal model demonstrating the above-described tolerance follows.

Rat pups were treated with nitroglycerin (NTG) approximately for 36–48 hours before performing bilateral carotid ligations. The dosing regimen for the 3 groups of rat pups used to generate the data was as follows.

Hair was removed from the abdominal region of the rat pup using a razor. One-quarter of a NTG patch (Minitran) was applied to the shaved area. A quarter patch of this size corresponds to a dose of 0.6 mg/24 hours (whole patch 2.4 mg/24 hr). Between 12 and 16 hours later, another quarter-patch was applied to the rat's abdomen, leaving the first on. This procedure was again repeated 12–16 hours later. Each rat pup received 3 or 4 quarter patches before surgery, which was performed two days later and consisted of bilateral carotid ligation followed by hypoxia to induce a stroke. Control animals did not receive NTG patches.

Using this procedure of inducing NTG systemic tolerance, the following results were obtained: In the control group, 7/11 (64%) of the animals suffered large (≦50%) cerebral cortical infarcts. In contrast, in the NTG-treated group, only ⅔13 (15%) of the animals had any discernible cerebral infarct at all (P<0.03 by Fisher's exact test). Thus, NTG was cerebral protective when administered in this fashion.

In more recent trials, the ¼ patch that is first applied is taken off 12–16 hr later, and two new ¼ patches are applied. 12–16 hr later, the two quarter patches are removed, and 3 new (¼) patches are applied. This may be repeated using 4 new (¼)=1 whole patch. In this fashion, the dose may be escalated to 2, 3 or more whole patches.

Animals are operated on (to induce a stroke) approximately 48 hr after the initial administration of NTG patches.

To convert the dosage given to rat pups in these experiments to a human dose of a NTG patch, the following approximation was used. First, the rat weight in grams is converted to surface area in square meters and the dose of NTG is calculated as dose per square meter. In general, the rat pups used here weighed ~20 grams, equivalent to approximately $5\times 10^{-3}$ square meters in surface area. Using a standard nomogram, the weight of a human (e.g., 60 kg) can be converted to square meters (~2 square meters for 60 kg). Thus, there is a scale factor in body area of 1:400 when converting rat to human dosage. In addition, the dose for a human per square meter would be approximately ¼ the dose per square meter given to a rat pup. Therefore, the human dose is approximately 100 times the rat dose, so that a patch containing 24 mg in the rat experiments is equivalent to a human patch containing about 240 mg. Such a human dose would have to be more slowly escalated to avoid initial hypotension with the first few NTG patch applications.

The compounds of the invention can be utilized to protect against a number of neurotoxic disorders associated with elevated levels or effects of glutamate or related compounds. Such disorders are mediated by stimulation of NMDA receptors or by downstream effects of NMDA receptor overstimulation. These disorders include ischemia, hypoxia, hypoglycemia, trauma to the nervous system, epilepsy, Huntington's disease, Alzheimer's disease, amyotrophic lateral sclerosis (ALS), Parkinson's disease, and other neurodegenerative disorders. Inherited or acquired chemical disorders mediated at least in part by NMDA receptor activation can also be treated. These include hyperammonemia, hepatic encephalopathy, hyperglycinemia, and others. See Tables 1 and 2. These include hyperammonemia, hepatic encephalopathy, hyperglycinemia and others (see Tables 1 and 2). Neuropathic pain syndromes such as causalgia may also be mediated in this manner and can be treated with the compounds of the invention. The method of the invention is particularly preferred for the treatment of the AIDS dementia complex (HIV-associated cognitive/motor complex plus incipient forms of cognitive, motor and sensory deficits not yet fulfilling the stringent criteria for these complexes) and other neurological manifestations of the AIDS virus (HIV-1 or HIV-2). The method may also be used for reduction of neuronal damage resulting from infection with other viruses, such as measles, which cause damage to the nervous system. Other diseases listed above can be treated.

One aspect of the invention features prolonged administration of increasing dosages of NO-generating compounds to establish tolerance of the vascular effects (coronary artery dilatation, blood pressure drop, etc.), thereby enabling higher dosages of the compounds for neuroprotection. One particular way to achieve this goal is to administer the NO-generating compound transdermally, using well established transdermal patch technology. Current transdermal nitroglycerin patches provide about 0.2–0.8 mg/hr. They have a typical surface area of 10 –30 cm². The standard protocol for the use of such patches limits their use to about 12 continuous hours to avoid systemic tolerance.

In order to establish systemic tolerance and thereby increase the NO-generating levels available for neuroprotection, a patient is started on a regime of therapy similar to that currently used for cardiac conditions (e.g., patch loaded with about 2–4 mg nitroglycerin to be used for about 10 hours, or about 0.2–0.4 mg/hr). This regime is followed continuously, without any substantial (no more than 4–6 hours) hiatus. Gradually (e.g., after a day), the dosage is increased, and blood pressure is monitored to be sure that systemic tolerance has been achieved. The rate of increase will depend on the patient, but it generally will involve doubling the dosage every 24 hours for a period of 2–3 days. Typically, levels of about 3–4 mg/hr will be achieved, but dosage could go as high as 2.5 gm/hr. Dosage can be increased by increasing the loading of existing patches, by increasing the surface area of similarly loaded patches, or by increasing the efficiency of permeability and the frequency of readministration of the patches. Those skilled in the art will appreciate that there are many ways to achieve the goal of systemic tolerance. In one specific method, color coded patches can be used to reduce the chance for misuse (e.g., red, then white, then blue). The colors would signify the sequence of use of the respective patches. The final patches would be designed to administer levels of NTG that are higher than any currently available patch can administer. For example, the final patch may have a size of 50 cm² or more; or it may be loaded to deliver over 3 mg/hr.

Those skilled in the art will appreciate that tolerance can also be achieved using slow release oral NTG (p.1166 of the 1992 PDR), or using ointments or other transdermal modalities.

Other Embodiments

The method described herein is useful for reducing neuronal injury in any mammal having NMDA receptors. Treatment of neuronal damage in humans is the preferred utility; but the method may also be employed successfully for veterinary purposes. The NO-generating compound may be co-administered with other redox compounds or enzymes to control superoxide ($O_2^{\bullet-}$)-related damage. Nitric oxide (NO•) is known to react with $O_2^{\bullet-}$ to form peroxynitrite ($ONOO^-$) which we have shown is toxic to neurons (see FIG. 7, above). Superoxide dismutase (SOD) plus catalase decrease the $O_2^{\bullet-}$ available for this reaction and therefore could enhance neuroprotection by allowing the NO reaction of nitrosation (transfer of $NO^+$ equivalents to thiol groups) to predominate to provide protection by down regulating the NMDA receptor's redox modulatory site. SOD plus catalase, or similarly acting compounds, can be administered with polyethylene glycol to enhance their absorption into the CNS and efficacy (Liu et al.,(1989) Am. J. Physiol. 256:589–593. An SOD mimic, the protein-bound polysaccharide of Coriolus versicolor QUEL, termed "PS-K", may also be effective by parenteral or oral routes of administration, especially with PEG to enhance CNS absorption. PQQ (pyrroloquinoline quinone—see U.S. Pat. No. 5,091,391, hereby incorporated by reference or PQQ's derivative esters or other quinones such as ubiquinone) could also be useful to accept an electron from NO• or from $O_2^{\bullet-}$ to drive the reaction toward nitrosation with NO+ equivalent species and hence toward neuroprotection.

Similarly, other useful agents either by themselves or as adjunctive agents (to be administered with nitroso-compounds) would limit NO• production (e.g., nitric oxide synthase (NOS) inhibitors). Such treatment would avoid peroxynitrite ($ONOO^-$) formation and hence neuronal injury, e.g., contribution to the AIDS dementia complex and other neurological manifestations of AIDS. These agents are listed in Table 3 (enclosed).

TABLE 1

Acute Neurologic Disorders with Neuronal Damage Thought to be Mediated at Least in Part by Excitatory Amino Acids* i. domoic acid poisoning from contaminated mussels
ii. cerebral ischemia, stroke
iii. hypoxia, anoxia, carbon monoxide poisoning
iv. hypoglycemia
v. prolonged epileptic seizures
vi. mechanical trauma to the nervous system
vii. Pb (lead) poisoning

*For general reviews, see Choi, Neuron 1:623–34 (1988); and Meldrum and Garthwaite, Trends Pharmacol. Sci. 11:379–387 (1990).

TABLE 2

Chronic Neurodegenerative Diseases with Neuronal Damage Thought or Proposed to be Mediated at Least in Part by Excitatory Amino Acids.* i. Neurolathyrism-BOAA (β-N-oxalylamino-L-alanine) in chick peas
ii. Guam Disease-BMAA (β-N-methyl-amino-L-alanine) in flour from cycad seeds
iii. Hungtington's disease
iv. ALS (amyotrophic lateral sclerosis)
v. Parkinsonism
vi. Alzheimer's disease
vii. AIDS dementia complex (HIV-associated cognitive/motor complex)
viii. Olivopontocerebellar atrophy (some recessive forms associated with glutamate dehydrogenase deficiency)
ix. Hepatic encephalopathy
x. Tourette's syndrome
xi. Mitochondrial abnormalities and other inherited biochemical disorders
   a. MELAS syndrome (mitochondrial myopathy, encephalopathy, lactic acidosis and stroke-like episodes)
   b. Rett syndrome

TABLE 2-continued

Chronic Neurodegenerative Diseases with Neuronal Damage Thought or Proposed to be Mediated at Least in Part by Excitatory Amino Acids.*

- c. homocysteinuria
- d. hyperprolinemia
- e. hyperglycinemia
- f. hydroxybutyric aminoaciduria
- g. sulfite oxidase deficiency

*For general reviews, see Choi, Neuron 1:623-34 (1988); and Meldrum and Garthwaite, Trends Pharmacol. Sci. 11:379-387 (1990).

TABLE 3

Nitric Oxide Synthase Inhibitors:

1. Arginine analogs including N-mono-methyl-L-arginine (NMA)
2. N-amino-L-arginine (NAA)
3. N-nitro-L-arginine (NNA)
4. N-nitro-L-arginine methyl ester
5. N-iminoethyl-L-ornithine
6. Diphenylene iodonium and analogs
   See, Steuhr, FASEB J 5:98-103 (1991)
7. Diphenyliodonium, calmodulin inhibitors such as trifluoparizine, calmidazolium chloride
8. Phospholipase A$_2$ inhibitors such as aristolochic acid
9. Calcineurin inhibitors, e.g., FK-506, cyclosporin A, and analogs including rapamycin (inhibit calcineurin and thus nitric oxide synthase by inhibiting its dephosphorylation)

APPENDIX A

METHOD OF PREVENTING NMDA RECEPTOR-MEDIATED NEURONAL DAMAGE

Background of the Invention

This application is a continuation-in-part of my earlier co-pending commonly owned application, U.S. Ser. No. 07/680,201, filed Apr. 4, 1991.

This invention relates to the therapies using the substance amantadine and related compounds particularly memantine and rimantidine.

Amantadine and/or related compounds have been proposed for various therapies. Initially, these compounds were proposed to treat influenza virus. For example, Mullis et al. U.S. Pat. No. 3,391,142 discloses adamantylamines which are said to be antiviral agents. Griffin U.S. Pat. No. 4,351,847 discloses that an amantadine derivative is effective against herpes simplex virus. Smith U.S. Pat. No. 3,328,251 discloses (at 13:24-31) that certain amantadine related compounds are effective against animal viruses, particularly swine influenza.

By chance, it was also observed that amantadine and related compounds are effective against the symptoms of Parkinson's disease. Tominack and Hayden (pp.460-461). See also, Scherm U.S. Pat. No. 4,122,193 at 6:54-60. Braunwald et al. (*Principles of Internal Medicine*, 11th ed., p. 2017, New York, McGraw Hill, 1987) report that amantadine has been used to treat Parkinson's disease and that its effect is achieved by its capacity to release stored dopamine from presynaptic terminals. See also Merk Index, p.55, #373; p. 1188, #8116; and APP-2, #A7, disclosing the use of various compounds for influenza A, treatment of Parkinsonism, and drug-induced extrapyramidal reactions;

one such compound is reportedly being studied in control of micturition and limb muscle mobility, as well as an antispasmodic.

Other uses for such compounds have been proposed. For example, Scherm '193 (at 6:56-60) discloses that certain compounds can be used for treating "other kinds of hyperkinesis [in addition to Parkinsonism] including head tremors, thalamic tension conditions and spastic conditions, and even for the activation of akinetic cerebroorganic conditions."

Bormann et al. U.S. Pat. No. 5,061,703 discloses certain amantadine derivatives are useful not only for the treatment of parkinsonian and parkinsonoid diseases, by a mode of action attributed to a dopaminergic influence on the central nervous system (2:38-3:17), but also to reduce neuronal damage associated with cerebral ischemia, which is mediated by the N-methyl-D-aspartate (NMDA) subtype of excitatory amino acid receptor. Bormann et al. reports that certain adamantine derivatives "... exhibit NMDA receptor channel-antagonistic and anticonvulsive properties." (2:61-63). It also reports (3:10-16) that the adamantine derivatives "are especially suited for the prevention and treatment of cerebral ischemia after apoplexy, open-heart surgery, cardiac standstill, subarachnoidal hemorrhage, transient cerebro-ischemic attacks, perinatal asphyxia, anoxia, hypoglycemia, apnoea and Alzheimer's disease. [Emphasis added.]"

Turski et al. (*Nature* 349:414, 1991), reports certain experiments investigating the role of excitatory amino acids in dopaminergic toxicity caused by intake of a toxin known as MPTP (1-methyl-4-phenyl-1,2,3,6,-tetra hydropyridine). Excitatory amino acid antagonists were coadministered with MPP$^+$ (the active metabolite of MPTP), and certain NMDA antagonists offered temporary protection against MPP$^+$.

Meldrum, Trends Pharm. Sci. September, 1990, vol. 11, pp. 379-387 reviews reported literature concerning the possibility that excitatory amino acid receptor agonists of endogenous or environmental origin contribute to neuronal degeneration in disease states. After reviewing the several known receptors implicated in excitatory amino acid activity (particularly glutamate activity), the authors review (p. 386) suggestions that excitotoxic mechanisms might play a role in the pathogenesis of various chronic neurodegenerative disorders including Huntington's disease, olivopontocerebellar atrophy, senile dementia of the Alzheimer type, parkinsonism and amyotrophic lateral sclerosis (ALS), as well as two chronic syndromes linked to plant toxins.

Rothman et al. Trends Neurosci. 10:299-302 (1987) also review literature concerning the possibility that glutamate neurotoxicity may be responsible for neuronal degeneration in various neurological disorders.

Bormann, Eur. J. Pharm. (1989) 166:591-592 reports that memantine blocks NMDA receptor channels.

Kornhuber et al. Eur. J. Pharm. 166:589-590 (1989) report that memantine inhibits the binding of an NMDA antagonist (MK-801) to post-mortem human brain homogenates.

Hahn et al. Proc. Nat'l Acad. Sci. (1988) 85:6556-6560 report that it is widely held that a glutamate-like toxin that resembles NMDA may be responsible for the death of nerve cells seen after severe neurological insults including stroke, seizures, and degenerative disorders, such as Huntington's disease, Alzheimer's disease, and the amyotrophic lateral sclerosis-parkinsonism-dementia complex found on Guam. They report findings suggesting that Ca$^{++}$ entry through NMDA-activated channels is responsible for this type of neuronal death and suggest strategies that may be clinically useful in the treatment of various neurological disorders.

Choi, Neuron 1:623–634 report that neurotoxicity due to excitatory amino acids may be involved in slowly progressive degenerative diseases such as Huntington's disease.

Summary of the Invention

In general, the invention features a method which, in contrast to Bormann '703, cited above, reduces receptor-mediated neuronal degeneration in a mammal in disease states which are non-ischemic. The method involves administering to the mammal a compound of the formula shown in FIG. 1' (or a physiologically acceptable salt thereof) wherein $R_1$ includes an amino group, and $R_2$-$R_{17}$ are independently H or a short chain aliphatic group including 1–5 carbons, and $R_4$ and $R_{10}$ (independently) may also be a halogen (particularly fluorine, chlorine or bromine) or an acyl group. The compound is administered in a concentration effective to cause such reduction in neuronal degeneration.

In preferred embodiments, $R_1$ is $NH_2$, and the compound is preferably amantadine; $R_4$ is a methyl group; $R_{10}$ is a methyl group; $R_4$ and $R_{10}$ are both methyl groups; $R_4$ and $R_{10}$ are both methyl groups and $R_1$ is $NH_2$, and the compound is preferably memantine.

Alternatively, $R_1$ may be

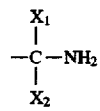

wherein $X_1$ and $X_2$ are independently H or a short chain aliphatic group including between 1–5 carbons [i.e., either a methyl group or between 1–4 ($-CH_2$) groups and a terminal methyl group]; $R_4$ is a methyl group; $R_{10}$ is a methyl group; $R_4$ and $R_{10}$ are methyl groups; $X_1$ and $X_2$ are H and $CH_3$, respectively, or $X_1$ and $X_2$ are $CH_3$ and H, respectively; and the compound is preferably rimantadine.

In various other preferred embodiments, the mammal is a human infected with a human immunodeficiency virus; the human manifests symptoms of the AIDS related complex or acquired immunodeficiency syndrome; the neurotoxicity is mediated (directly or indirectly) by an excitatory amino acid, or a structurally similar compound such as quinolinate, which leads to the activation of an NMDA receptor-operated ionic channel; for example, the neurotoxicity is mediated by glutamate, aspartate, homocysteic acid, cysteine sulphinic acid, cysteic acid, quinolinate, or N-acetyl aspartyl glutamate.

By "non-ischemic, long-term NMDA receptor-mediated neuronal degeneration" is meant progressive neuronal injury over a long period of time as a result of stimulation or costimulation of the NMDA receptor. In particular, I mean to include the neurodegeneration associated with long term disease states such as Huntington's disease, Alzheimer's disease, amyotrophic lateral sclerosis (ALS, which is also known as motor neuron disease), acquired immunodeficiency (AIDS). Other conditions that may be treated in accordance with the invention include: neurolathyrism (resulting from β-N-oxalyamino-L-alanine found in chick peas); "Guam disease" (resulting from β-N-methyl-amino-L-alanine found in flour from cycad seeds); and olivopontocerebellar atrophy. The invention also includes therapies for certain mitochondrial abnormalties or inherited biochemical disorders including: MELAS syndrome (mitochondrial myopathy, encephalopathy, lactic acidosis and stroke-like episodes); Rett syndrome; homocysteinuria; hyperprolinemia; hyperglycinemia (non-ketotic); hepatic encephalopathy; uremic encephalopathy; and 4-hydroxybuturic aciduria. The invention also includes treating peripheral neuropathy, especially painful types of peripheral neuropathy which may be of central nervous system origin. The invention also includes treating certain acute conditions including trauma (e.g., spinal, brain or eye trauma) carbon monoxide poisoning; lead poisoning; or domoic acid poisoning (domoic acid is a glutamate-like agonist found in contaminated muscles).

Useful compounds of the instant invention include a tricyclic 10 carbon ring which includes at least one amino group at position $R_1$ of the general formula shown in FIG. 1'. The amino group may be attached directly to a ring carbon (as is the case for amantadine; see FIG. 2a'), or it may be attached to a carbon attached to the carbon ring (as is the case for rimantadine; see FIG. 2b'). $R_2$-$R_{17}$ (of the general formula of FIG. 1') are hydrogen atoms, methyl groups, or short chain aliphatic groups which include between 1–5 saturated carbons [i.e., 1–4 ($-CH_2$) groups and a terminal methyl group], or any combination, thereof. The neuroprotective potency of the compounds may be enhanced by substitutions of ring hydrogens. In one example, methyl group substituants at positions $R_4$ and $R_{10}$ (of the general formula shown in FIG. 1') greatly enhance the ability and potency of the compound, memantine (shown in FIG. 2c'), to prevent glutamate-induced neuronal damage. Memantine is neuroprotective in vitro at a concentration of 2–12 μM (see below); amantadine, a molecule unsubstituted at these positions, is effective at a concentration of approximately 200 μM. The water solubility of compounds of the general formula shown in FIG. 1' may be increased by formulating the compound into a physiologically-acceptable salt, e.g., by reaction with HCl.

The preferred compounds of the invention (i.e., amantadine, rimantadine, and memantine, and similar derivatives) are water soluble and are able to pass readily through the blood brain barrier, facilitating a therapy which is both extremely rapid and unusually potent. The preferred compounds also provide the advantage of a proven record of safe human administration (i.e., for treatment of viral infections or for treatment of Parkinson's disease, but not neuronal degeneration of Parkinsonism). For example, amantadine has been approved for use by human patients, at least, in the United States. Disorders which may be treated by the method of the invention are listed above in this application.

Another aspect of the invention features methods of screening compounds to identify those with an increased prospect for safety and efficacy, by selecting NMDA receptor channel complex antagonists characterized in that they operate quickly and quickly cease operation after administration of the compound ceases, and in that they require the presence of an NMDA-excitatory compound in order to block activity. According to this second aspect of the invention candidate NMDA channel antagonists are preliminarily screened for safety and efficacy by: (a) assessing the time period required for the candidate to induce blockade of NMDA-receptor-associate ion channels; (b) assessing the time period required for loss of blockade of ion channels when administration of the compound ceases; and (c) assessing the ability of the compound to block NMDA mediated current in the absence of an NMDA-excitatory compound. Compounds selected are those with time periods (a) and (b) that are shorter than the time periods characteristic of MK-801 and with a substantially negative result in step (c), above, thereby enhancing the prospect that the candidate will be a clinically tolerated selective NMDA antagonist. Those compounds are then tested to verify that they protect against NMDA mediated neurotoxicity.

19

Other features and advantages of the invention will be apparent from the following detailed description and from the claims.

Detailed Description

The drawings are first briefly described.

Drawings FIG. 1' is the general formula of the compounds useful in the method of the invention.

FIG. 2a', 2b', and 2c are schematic representations of (a) amantadine, (b) rimantadine, and (c) memantine, respectively.

FIG. 3' is a graphical representation showing that memantine prevents glutamate-mediated retinal ganglion cell neurotoxicity.

FIGS. 4A'-4B' are representations of results of patch clamp experiments described below.

The present invention is based on the finding that the amantadine derivative memantine (1-amino-3,5-dimethyl adamantine) reduces neuronal damage (see below); and that this reduction in damage is due to a block of NMDA receptor-operated channel activation by excitatory amino acids (such as glutamate-related compounds) using concentrations of memantine that are readily obtainable in human patients taking the drug (Wesemann et al., *J. Neural Transmission* (Supp.) 16:143, 1980). An increased level of one or more glutamate-related compounds is associated with many neurodegenerative disorders (e.g., those listed above), and amantadine derivatives are therefore useful for their treatment. In addition to glutamate itself, neuronal injury may result from stimulation of the NMDA receptor by other excitatory amino acids or structurally similar compounds; examples of such compounds are aspartate, homocysteic acid, cysteine sulphinic acid, cysteic acid, and quinolinate. Neuronal injury may also result from stimulation by excitatory peptides, such as N-acetyl aspartyl glutamate.

Other compounds structurally related to memantine are also preferred for use in the invention. By "structurally related" is meant a compound composed of a tricyclic 10 carbon ring bearing an amino group. Such compounds include, but are not limited to, amantadine (1-adamantanamine hydrochloride) itself and rimantadine (alpha-methyl-1-adamantanemethylamine hydrochloride).

Compounds of the invention (i.e., those of the general formula shown in FIG. 1' and including compounds bearing substitutions predicted to increase potency) may be tested for efficacy in reducing neuronal damage using the assay described below; an effective compound will cause a decrease in neuronal cell death. Compounds most preferred in the invention are those which effect the greatest protection of neurons from NMDA receptor-mediated injury, e.g., that injury resulting from stimulation of the NMDA receptor by glutamate (as shown below) or other excitatory amino acids or structurally similar compounds or from stimulation by excitatory peptides, such as N-acetyl aspartyl glutamate.

Assay for Neuronal Cell Function and Death

To test amantadine derivatives for their ability to prevent neurotoxicity, neuronal cell death may be assayed as follows. Under general anesthesia, the fluorescent dye granular blue (Mackromolecular Chemin, Umstadt, FRG) is injected as approximately a 2% (w/v) suspension in saline into the superior colliculus of 4- to 6-day-old Long-Evans rats (Charles River Laboratory, Wilmington, Mass.). Two to 6 days later, the animals are sacrificed by decapitation and enucleated, and the retinas quickly removed. The retinas are dissociated by mild treatment with the enzyme papain and cultured in Eagle's minimum essential medium (MEM,

20 catalog #1090, Gibco, Grand Island, N.Y.) supplemented with 0.7% (w/v) methylcellulose, 0.3% (w/v) glucose, 2 mM glutamine, 1 µg/ml gentamicin, and 5% (v/v) rat serum, as described in Lipton et al., *J. Physiol.* 385:361, 1987. The cells are plated onto 75 mm$^2$ glass coverslips coated with poly-L-lysine in 35 mm tissue culture dishes. The candidate amantadine derivative is added (e.g., in a series of concentrations ranging from 1 nM–1 mM) in the presence or absence of compounds which activate the NMDA receptor-operated channel complex, and in high calcium, low magnesium medium (10 mM $CaCl_2$, 50 µM $MgCl_2$) to enhance NMDA-receptor neurotoxicity in this preparation (Hahn et al., *Proc. Natl. Acad. Sci. USA* 85:6556, 1988; Levy et al., *Neurology* 40:852, 1990; Levy et al., *Neurosci. Lett.* 110:291, 1990). The degree of survival (under these ionic conditions or with added exogenous NMDA (200 µM))is compared to that in normal medium (1.8 mM $CaCl_2$, 0.8 mM $MgCl_2$), which minimizes NMDA receptor-mediated injury in this preparation (Hahn et al., cited above). Incubations last 16–24 h at 37° C. in an atmosphere of 5% $CO_2$/95% air. The ability of retinal ganglion cells to take up and cleave fluorescein diacetate to fluorescein is used as an index of their viability as described in detail in Hahn et al. (*Proc. Natl. Acad. Sci. USA* 85:6556, 1988). Dye uptake and cleavage generally correlate well with normal electrophysiological properties assayed with patch electrodes.

To perform the viability test, the cell-culture medium is exchanged for physiological saline containing 0.0005% fluorescein diacetate for 15–45 s, and then cells are rinsed in saline. Retinal ganglion cell neurons that do not contain the fluorescein dye (and thus are not living) often remain visible under both phase-contrast and UV fluorescence optics, the latter because of the continued presence of the marker dye granular blue; other dead retinal ganglion cells disintegrate, leaving only cell debris. In contrast, the viable retinal ganglion cells display not only a blue color in the UV light but also a yellow-green fluorescence with filters appropriate for fluorescein. Thus, the use of two exchangeable fluorescence filter sets permits the rapid determination of viable ganglion cells in the cultures. The ganglion cells are often found as solitary neurons as well as neurons lying among other cells in small clusters.

An amantadine derivative may be tested for utility in the method of the invention using any type of neuronal cell from the central nervous system, as long as the cell can be isolated intact by conventional techniques. In addition to the retinal cultures described above, we have also used hippocampal and cortical neurons, but any neuron can be used that possess NMDA receptors (e.g., neurons from other regions of the brain). Such neurons may be prenatal or postnatal, and they may be from a human, rodent or other mammals. In one example, retinal cultures can be produced from postnatal mammals; they are well-characterized and contain a central neuron, the retinal ganglion cell, that can be unequivocally identified with fluorescent labels. A substantial portion of retinal ganglion cells in culture display both functional synaptic activity and bear many, if not all, of the neurotransmitter receptors found in the intact central nervous system.

There now follows an example of an amantadine derivative useful in the method of the invention and an illustration of its efficacy in reducing neuronal damage. This example is provided to illustrate the invention and should not be construed as limiting.

Memantine Prevents NMDA Receptor-Mediated Neurotoxicity

Using the assay described above, the amantadine derivative, memantine, was tested for its ability to increase survival of glutamate-treated retinal ganglion cells. In eight separate experiments, retinal ganglion cells were cultured in either normal medium (i.e., MEM containing 1.8 mM $CaCl_2$, 0.8mM $MgCl_2$) or in high calcium, low magnesium medium (i.e., 10 mM $CaCl_2$, 50 μm $MgCl_2$). The latter medium is known to enhance NMDA receptor-mediated neurotoxicity due to an endogenous glutamate receptor agonist (Hahn et al., *Proc. Natl. Acad. Sci. USA* 85:6556, 1988; Levy et al., *Neurology* 40:852, 1990; Levy et al., *Neurosci. Lett.* 110:291, 1990). Memantine HCl was diluted in double-distilled water, filtered, and added to the growth media (to a final concentration of between 1 μM–25 μM). The retinal cells were incubated for 16–20 hours at 37° C. in a humidified atmosphere of 5% $CO_2$ and 95% air.

As shown in FIG. 3', an endogenous glutamate-like agonist produces retinal cell neurotoxicity in the presence of elevated extracellular calcium concentrations (compare FIG. 3', columns 1 and 2). To verify that the agonist was glutamate-related, the enzyme glutamate-pyruvate transaminase (GPT; 0.25 mg/ml; Boehringer-Mannheim, Indianapolis, Ind.) was added; this enzyme specifically degrades endogenous glutamate by transaminating it to α-keto-glutamate in the presence of pyruvate. Under these conditions, survival of retinal ganglion cells was enhanced; i.e., an approximately equal number of neurons survived in the high calcium, low magnesium medium plus GPT and pyruvate (2 mM) as survived in the control cultures in normal medium. This finding indicated that the endogenous toxin was glutamate itself. HPLC analysis verified the breakdown of glutamate by GPT.

The amantadine derivative, memantine, prevented retinal ganglion cell death from the endogenous glutamate-related toxin in a dose-dependent manner (FIG. 3'). Increased neuronal survival at 6 μM memantine (FIG. 3', column 4) reached statistical significance compared to the control (FIG. 3', column 1). All experiments depicted in FIG. 3' involving memantine treatment were repeated in triplicate and normalized to control cultures (i.e., normal medium lacking memantine). The values depicted represent mean+ standard error of the mean (SEM). An analysis of variance was used to test for significance; this analysis was followed by a Scheffé test for multiple comparison of means (Hahn et al., 1988, supra).

These data indicate that memantine blocks neuronal cell death mediated by excessive stimulation of the NMDA receptor. Without being bound to any theory as to the mechanism whereby memantine exerts its neuroprotective effect, it is possible that memantine blocks the glutamate-induced increase in intracellular $Ca^{2+}$ at the NMDA receptor-associated ionic channel. By analogy with MK-801 (dizocilpine; an NMDA-specific antagonist), the mode of action of memantine may be an un-competitive inhibition of $Ca^{2+}$ influx by blocking the NMDA receptor-operated channels. If so, inhibition by memantine is contingent upon prior activation of the receptor by the agonist. This has important consequences at the therapeutic level. Normal NMDA receptor activation (for example, that involved in long-term potentiation, a form of learning and memory) may be unaffected by the compounds of the invention while neuronal injury resulting from escalating levels of glutamate or other excitatory compounds might be effectively blocked (Karschin et al., *J. Neurosci.* 8:2895, 1988; Levy and Lipton, *Neurology* 40:852, 1990). Memantine analogs have undergone clinical trials in the United States and in the Soviet Union using therapeutic doses for influenza A therapy. Those studies revealed only limited and reversible central nervous system side effects (Tominack et al., *Infect. Dis. Clin. N. Am.* 1: (2):459, 1987; Clover et al., *Am. J. Dis. Child.* 140:706, 1986; Hall et al., *Pediatrics* 80(2):275, 1987; Zlydnikov et al, *Reviews of Infect. Dis.* 3(3):408, 1981; Dolin et al, *New Eng. J. Med.* 302:580, 1982). There has been one case report of visual loss in an adult patient who had been treated for Parkinson's symptoms with amantadine for several weeks. However, full visual acuity returned after drug discontinuation (Perlman et al., *JAMA* 237:1200, 1977).

In selecting other NMDA channel complex blockers within the scope of the above invention, it is important to understand the implications of the above memantine data. First, it is useful to select an uncompetitive NMDA inhibitor—i.e., one whose inhibitory activity is contingent on prior activation of the receptor by a receptor agonist. Second, it is useful to select NMDA inhibitors that operate quickly and are quickly reversed upon cessation of administration of the drug. This strategy maximizes normal CNS function and reduces side effects.

As shown by the following examples memantine's kinetics for blocking/unblocking NMDA receptor-mediated response are relatively rapid.

FIGS. 4A'–4B' depict evidence for open-channel block of NMDA-elicited whole-cell current by memantine (MEM) on rat retinal ganglion cells. FIG. 4a' shows a blocking effect of 12 μM memantine on 200 μM NMDA-induced current at holding potentials of −50 and +50 mV in whole-cell recordings. FIG. 4b' shows a lack of effect on 200 μM NMDA-induced current of 12 μM memantine when administered alone at −60 mV (left). When coapplied with agonist, 12 μM memantine did not affect the current elicited by 50 μM kainate (KA) or 5 μM quisqualate (QUIS), whereas the response to 200 μM NMDA was inhibited by 90% at −60 mV (n=17) (right). A rapid application system was used to administer the drugs, and a fast washout method was used in the experiments shown in FIGS. 4A' and 4B'.

The above experiments were performed as follows.

Cell Culture

For retinal ganglion cell labeling, dissociation, and culture, we used techniques that have been detailed elsewhere (Leifer et al. (1984) *Science* 224:303–306). Briefly, retinal ganglion cells of 4-6-d-old Long-Evans rats were retrogradely labeled with granular blue by injection in the superior colliculus and retrograde transport. Two to six days later, the animals were killed by decapitation. Following enucleation, the retinas were dissociated with mild treatment with the enzyme papain. The retinal cells were than plated onto glass coverslips coated with poly-L-lysine in 35 mm tissue culture dishes. The growth medium was Eagle's minimum essential medium supplemented with 0.7% (w/v) methylcellulose, 0.3% (w/v) glucose, 2 mM glutamine, 5% (v/v) rat serum, and 1 μg/ml gentamicin. Retinal ganglion cells were identified by the presence of the retrogradely transported dye granular blue.

Patch-Clamp Electrophysiology

Whole-cell and single-channel recordings of rat retinal ganglion cells were performed as described in detail elsewhere (Hamill et al., 1981; Lipton and Tauck, 1987). The neurons were continuously superfused in a chamber at 27°–29° C. with a bath solution composed of (in mM) NaCl, 137.6; KCl, 5.8; $CaCl_2$, 2.5; HEPES, 5; glucose, 22.2; with phenol red, 0.001% (v/v); glycine, 1 μM; pH 7.2; and no added magnesium. The patch pipettes were filled with an intracellular solution containing (in mM) CsCl, 120; tetraethylammonium chloride, 20; HEPES, 10; EGTA, 2.25; $CaCl_2$, 1; and $MgCl_2$, 2; and sometimes with 3 mM Mg-ATP to minimize rundown in prolonged recordings (pH 7.2). The agonists and antagonists were prepared in bath solution containing 1 µM tetrodotoxin (TTX). and they were applied by an array of pneumatic pipettes placed 20–50 µm from the neurons. Solution changes could be achieved rapidly. within 50–100 msec. by moving the array of constantly flowing pipette tips relative to the cell with a micromanipulator driver. A control pipette containing bath solution and 1 µM TTX was used to wash out NMDA-induced current rapidly.

Therapy

To prevent neuronal damage. amantadine and its derivatives may be administered by any of a number of routes in an amount sufficient to block glutamate's effect on the NMDA receptor. The amantadine derivative may be included in a pharmaceutical preparation, using a pharmaceutical carrier (e.g., physiological saline); the exact formulation of the therapeutic mixture depends upon the route of administration. Preferably, the compound is administered orally or intravenously, but it may also be administered intrathecally or intravitreally. The preferred compounds, amantadine, memantine, and rimantadine are administered at 100–500 µg/day, 5–80 mg/day, and 50–300 mg/day, respectively, in divided doses. Any other compound, determined to be an effective neuroprotective agent by the assays described herein, is administered orally, intravenously, intrathecally, or intravitreally at 100 µg-500 mg/day in divided doses. Treatment may be repeated as necessary to prevent or alleviate neurological injury. The compounds of the invention can be utilized to protect against slow progressive neurodegeneration associated with a number of disorders described above in this application.

The method of the invention is particularly preferred for the treatment of AIDS dementia and other neurological manifestations of the AIDS virus (HIV-1, HIV-2, and other forms of the virus). The method may also be used for reduction of neuronal damage resulting from infection with other viruses which cause damage to the nervous system. The invention also features treating acute and chronic neurodegenerative disorders described above.

Other Embodiments

The method described herein is useful for reducing neuronal injury in any mammal having NMDA receptors. Treatment of neuronal damage in humans is the preferred utility; but the method may also be employed successfully for veterinary purposes.

Abstract of the Disclosure

Disclosed is a method for reducing non-ischemic NMDA receptor-mediated neuronal damage in a mammal by administering to the mammal a compound of the formula shown in FIG. 1' (or a physiologically-acceptable salt thereof), wherein $R_1$ includes an amino group, $R_2$–$R_{17}$ are independently H or a short chain aliphatic group comprising 1–5 carbons, and $R_4$ and $R_{10}$ also may (independently) be a halogen or an acyl group. Also disclosed is a screen for antagonists of NMDA receptor mediated neurotoxicity which have an enhanced prospect for being clinically tolerated and selective against such neurotoxicity.

Figure 1:
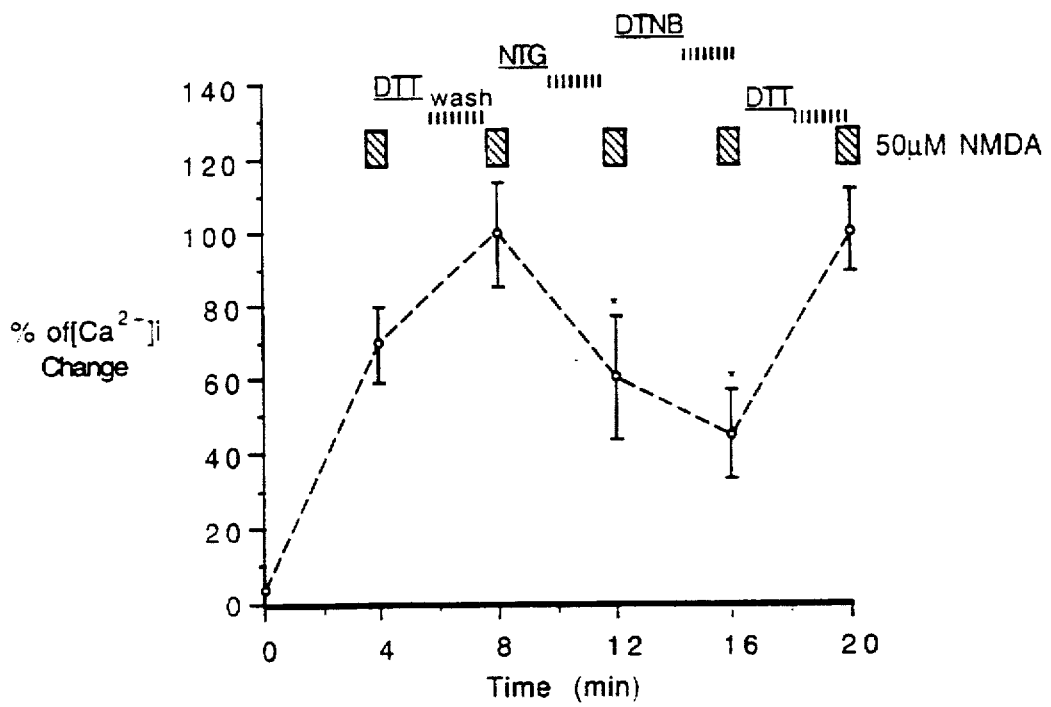
Figure 2:
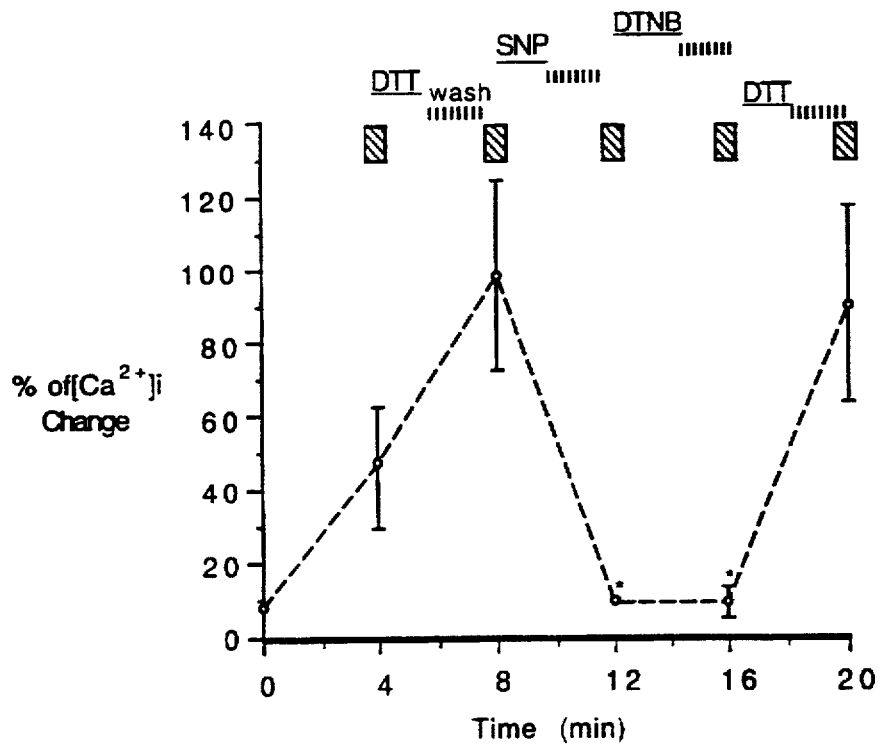
Figure 3:
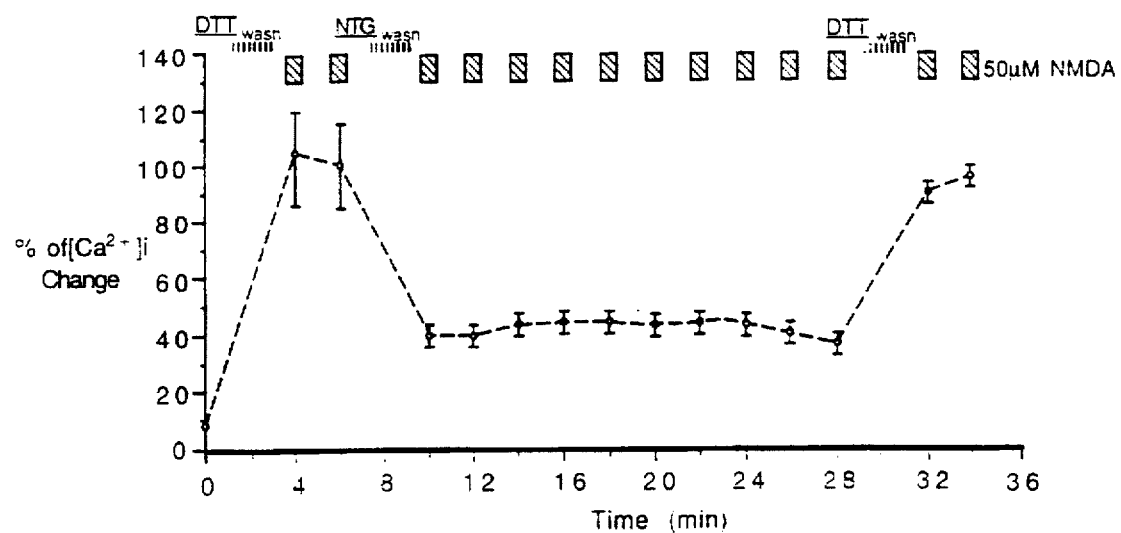
Figure 4:
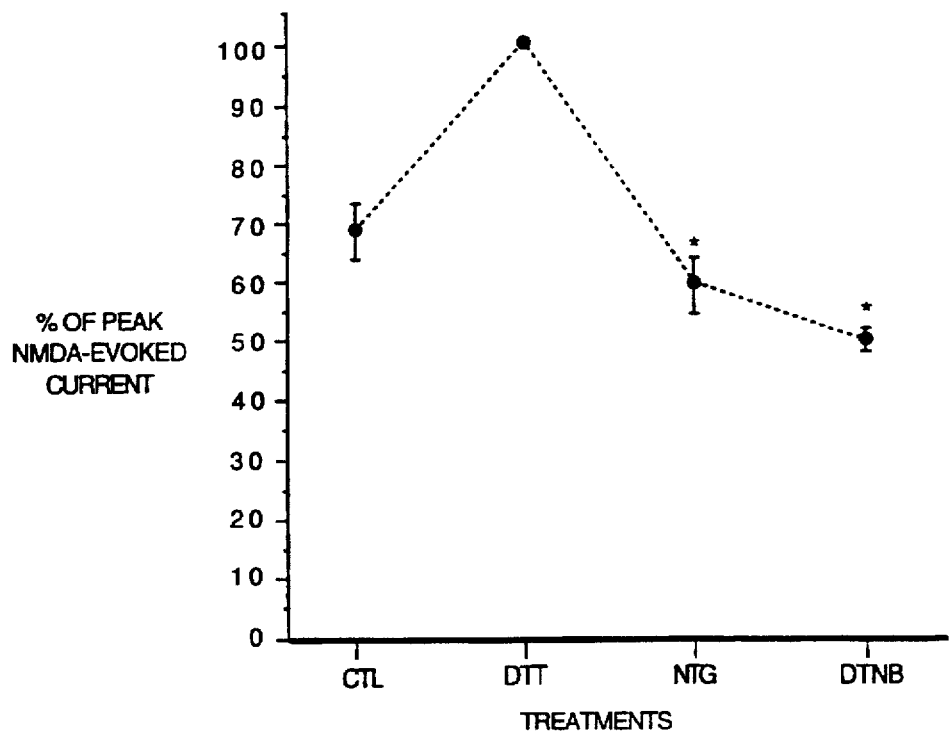
Figure 5A:
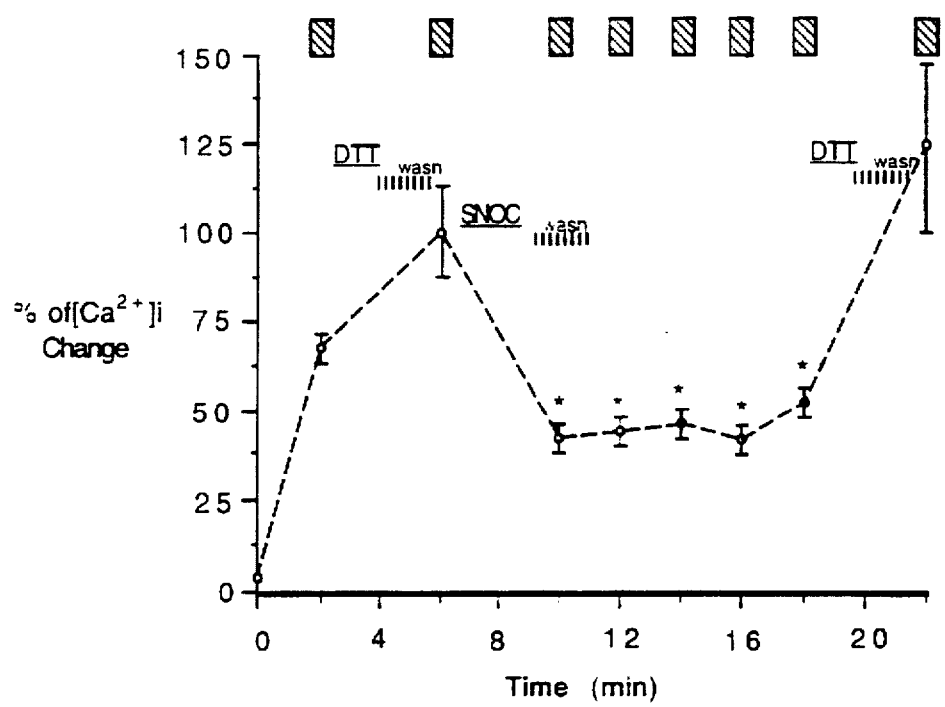
Figure 5B:
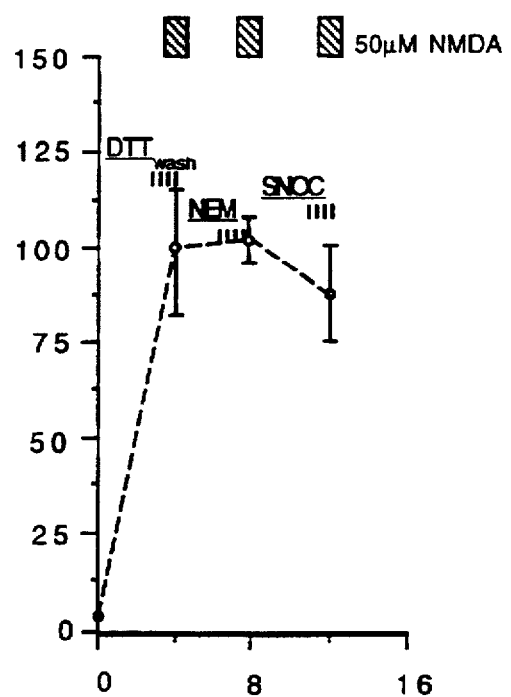
Figure 6A:
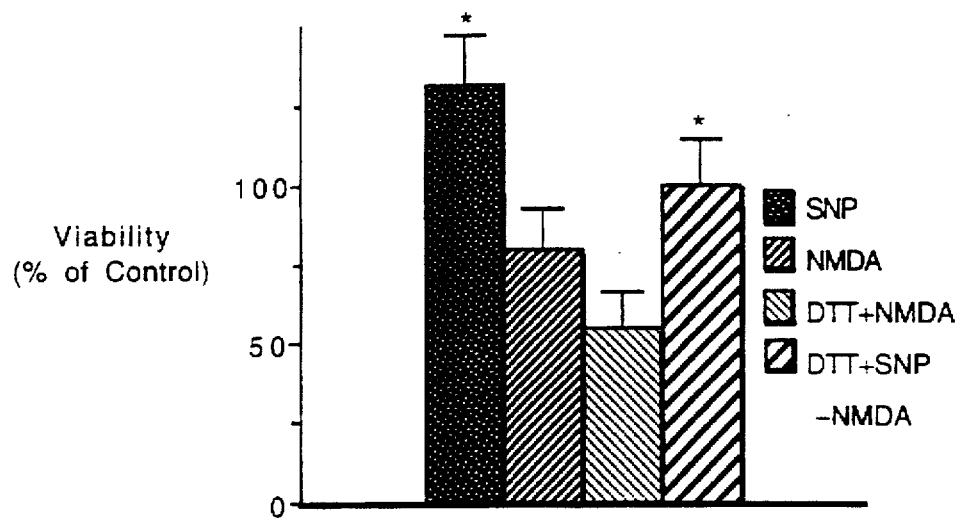
Figure 6B:
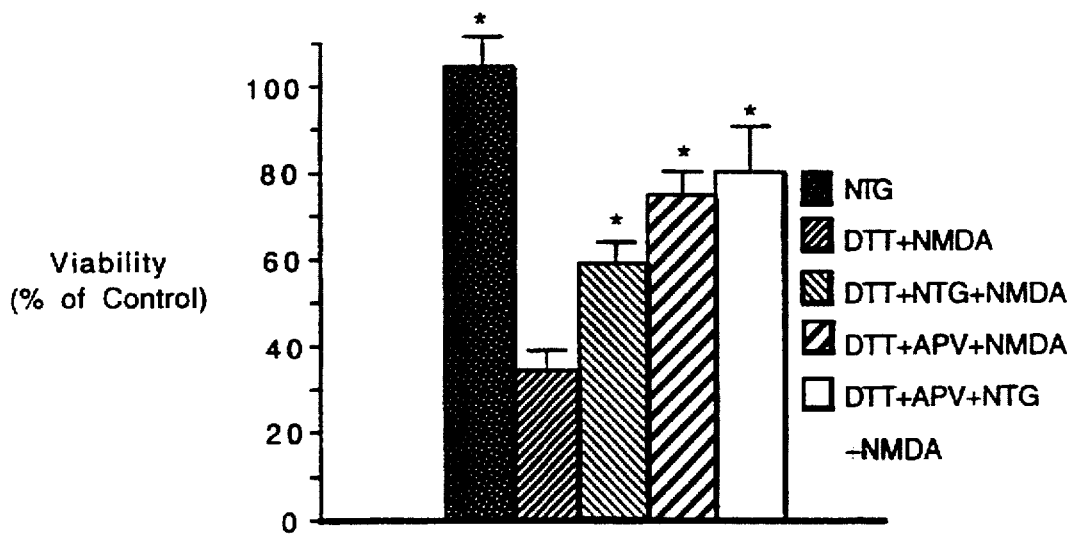
Figure 7A:
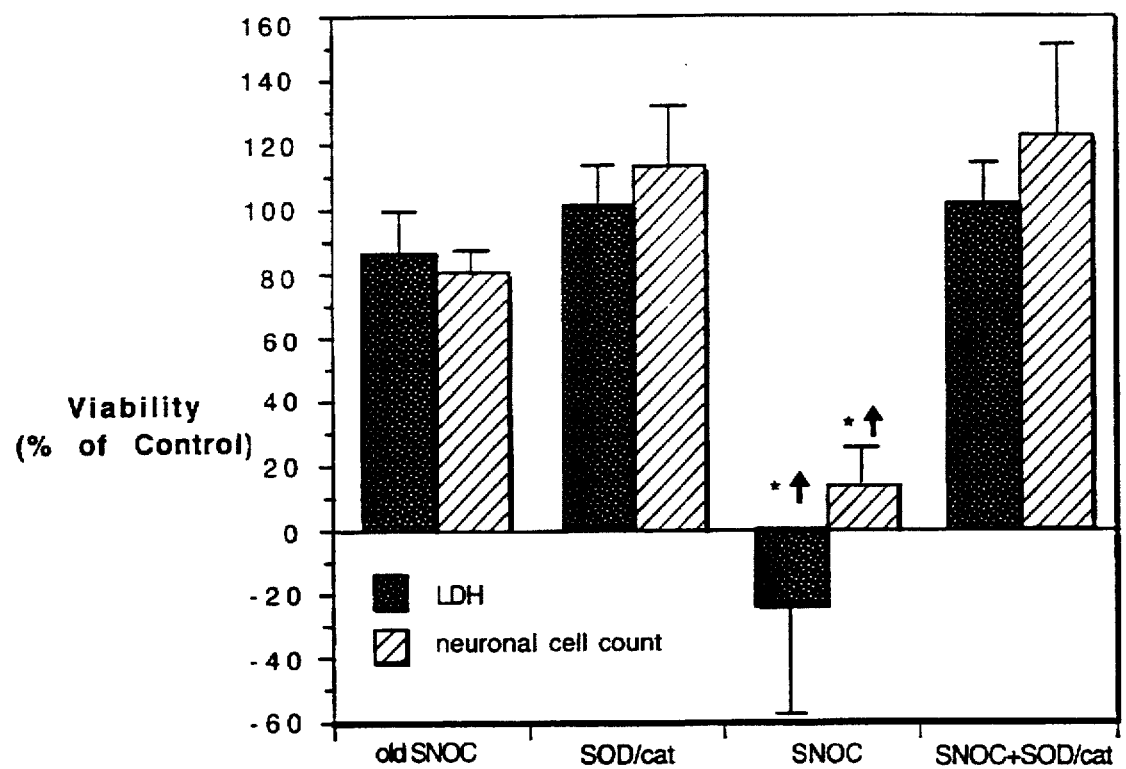
Figure 7B:
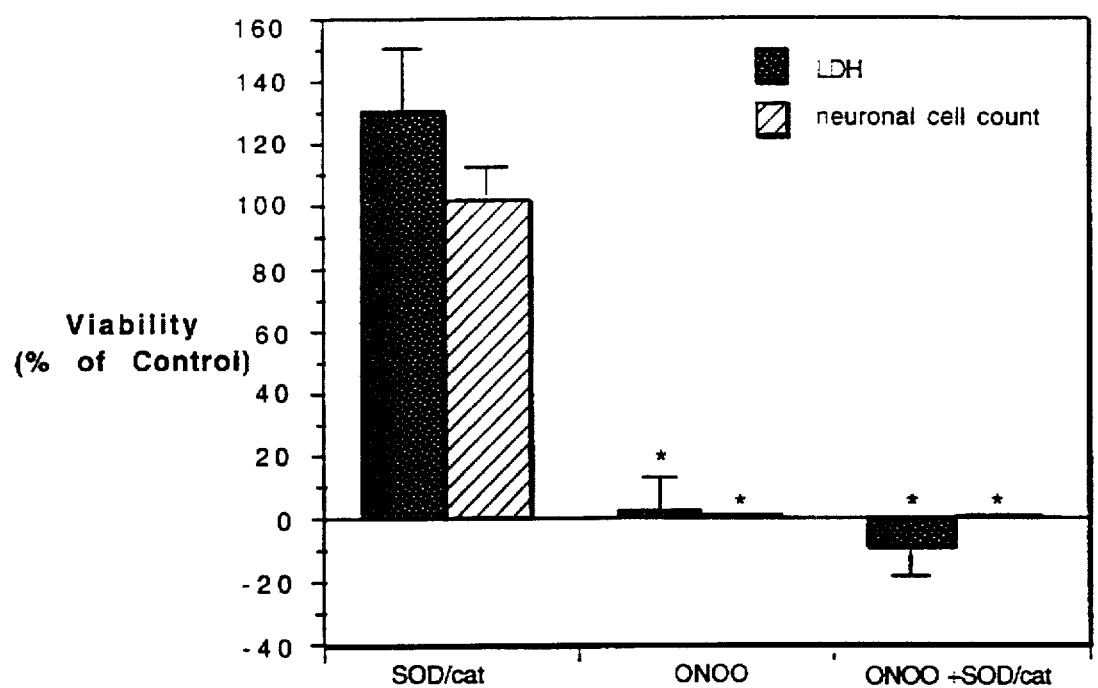

I claim:

1. A method for a preliminary screen of candidate NMDA channel antagonists for safety and efficacy, said method comprising
   a) determining the time period required for the candidate to induce blockade of NMDA-receptor-associate ion channels;
   b) determining the time period required for loss of said blockade of ion channels when administration of the compound ceases; and
   c) selecting a compound with time periods (a) and (b) that are shorter than the time periods characteristic of MK-801, thereby enhancing the prospect that the candidate will be a clinically tolerated selective NMDA antagonist.

* * * * *

UNITED STATES PATENT AND TRADEMARK OFFICE
CERTIFICATE OF CORRECTION

PATENT NO.    : 5,747,545
DATED         : MAY 5, 1998
INVENTOR(S)   : STUART A. LIPTON

It is certified that error appears in the above-identified patent and that said Letters Patent is hereby corrected as shown below:

At column 1, line 4, before "BACKGROUND OF THE INVENTION" insert --This invention was made with government support under Grant No. R01 EY09024 by the NIH. The government has certain rights in the invention.--

Signed and Sealed this

Twelfth Day of September, 2000

Attest:

Q. TODD DICKINSON

Attesting Officer

Director of Patents and Trademarks